United States Patent
Mountford et al.

(10) Patent No.: US 9,677,051 B2
(45) Date of Patent: Jun. 13, 2017

(54) ERYTHROID PRODUCTION

(71) Applicants: The Common Services Agency, Edinburgh (GB); University Court Of The University Of Glasgow, Glasgow (GB)

(72) Inventors: Joanne Mountford, Glasgow (GB); Emmanuel Oliver, Glasgow (GB)

(73) Assignees: The Common Services Agency, Edinburgh (GB); University Court of the University of Glasgow, Glasgow (GB)

(*) Notice: Subject to any disclaimer, the term of this patent is extended or adjusted under 35 U.S.C. 154(b) by 0 days.

(21) Appl. No.: 14/415,856

(22) PCT Filed: Jul. 18, 2013

(86) PCT No.: PCT/GB2013/051917
§ 371 (c)(1),
(2) Date: Jan. 20, 2015

(87) PCT Pub. No.: WO2014/013255
PCT Pub. Date: Jan. 23, 2014

(65) Prior Publication Data
US 2015/0203818 A1 Jul. 23, 2015

(30) Foreign Application Priority Data

Jul. 20, 2012 (GB) .................................. 1212960.7

(51) Int. Cl.
*C12N 5/00* (2006.01)
*C12N 5/02* (2006.01)
*C12N 15/00* (2006.01)
*C12N 5/078* (2010.01)

(52) U.S. Cl.
CPC ........ *C12N 5/0641* (2013.01); *C12N 2501/01* (2013.01); *C12N 2501/113* (2013.01); *C12N 2501/125* (2013.01); *C12N 2501/155* (2013.01); *C12N 2501/16* (2013.01); *C12N 2501/165* (2013.01); *C12N 2501/39* (2013.01); *C12N 2501/40* (2013.01); *C12N 2501/415* (2013.01); *C12N 2501/727* (2013.01); *C12N 2501/999* (2013.01); *C12N 2506/02* (2013.01); *C12N 2506/45* (2013.01)

(58) Field of Classification Search
CPC .............. C12N 5/0641; C12N 2506/00; C12N 2506/02
See application file for complete search history.

(56) References Cited

FOREIGN PATENT DOCUMENTS

WO WO 2006/072016 A2 7/2006
WO WO 2009/137629 A2 11/2009

OTHER PUBLICATIONS

Cheng (2008, Development, 135:3447-3458).*
Mountford (2011, Transfusion and Apheresis Science, 45:58-89).*
Lu (2008, Blood, 112:4475-4484).*
Olivier (2016, ISSCR Annual Meeting, Stockholm Sweden, Poster Abstract Book, p. 38, W-1088).*
Thomson et al. (PNAS, 92:7844-7848 (Aug. 1995).*
NIH (Stem Cells: Scientific Progress and Future Research Directions, Department of Health and Human Services, Chapter 1, pp. 14, Jun. 2001).*
Anstee et al. "Production of erythroid cells from human embryonic stem cells (hESC) and human induced pluripotent stem cells (hips)", *Transfusion Clinique et Biologique* 17(3):104-109 (2010).
Ebihara et al. "Generation of red blood cells from human embryonic/induced pluripotent stem cells for blood transfusion", *Int. J. Hematol.* 95(6):610-616 (2012).
Huber "Dissecting hematopoietic differentiation using the embryonic stem cell differentiation model", *Int. J. Dev. Biol.* 54(6-7):991-1002 (2010).
Lapillonne et al. "Red blood cell generation from human induced pluripotent stem cells: perspectives for transfusion medicine", *Haematologica* 95(10):1651-1659 (2010).
Notification of Transmittal of the International Search Report and the Written Opinion of the International Searching Authority, or the Declaration corresponding to International Application No. PCT/GB2013/051917 mailed Oct. 18, 2013.

* cited by examiner

*Primary Examiner* — Valarie Bertoglio
(74) *Attorney, Agent, or Firm* — Myers Bigel, P.A.

(57) ABSTRACT

This invention provides method and media suitable for inducing and supporting the differentiation of stem cells into erythroid cells.

19 Claims, 18 Drawing Sheets

Figure 1:
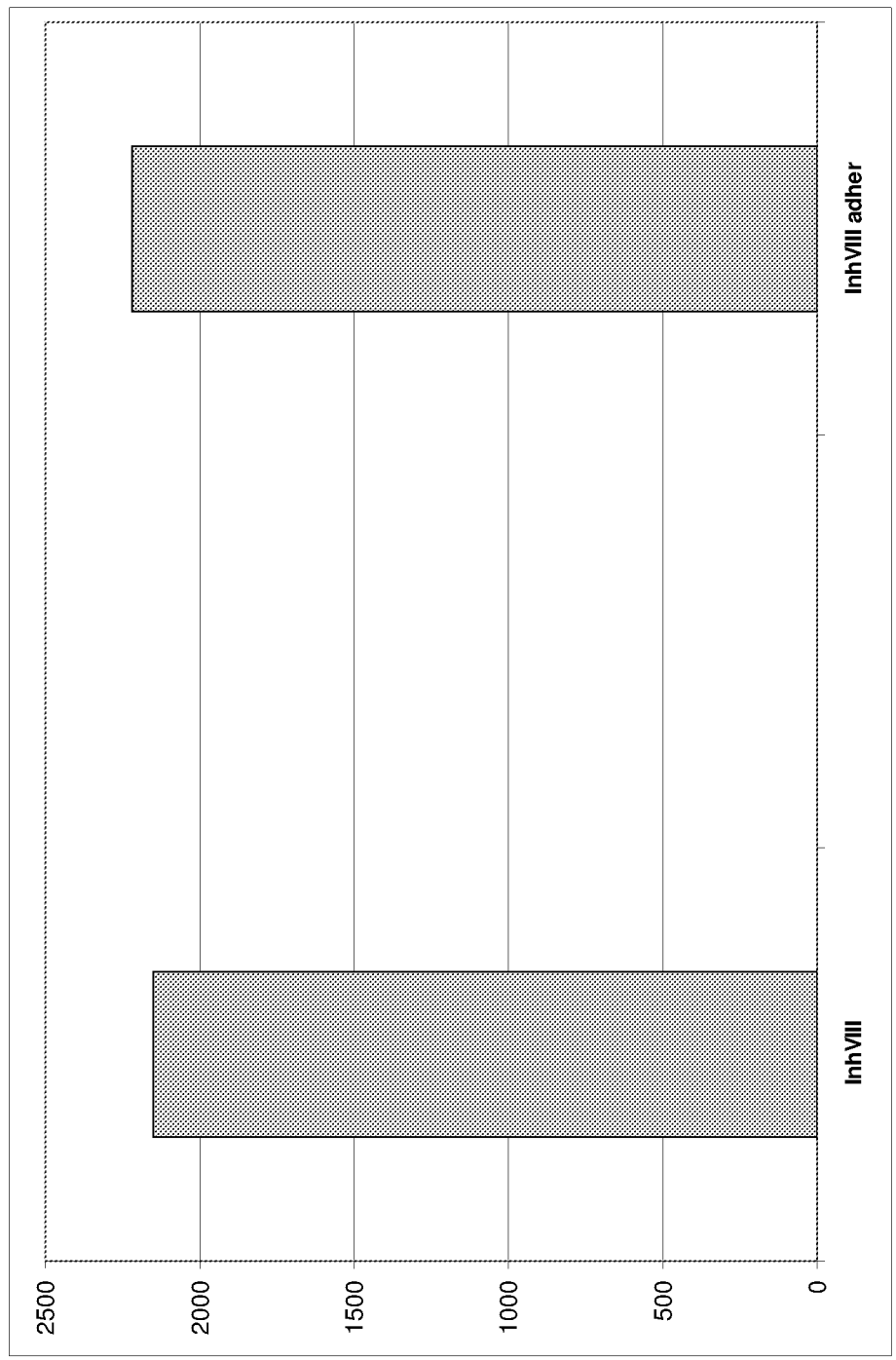

Globins from H1 hESC derived erythroid cells
(ζ undetectable and ε greatly reduced)

Globins from fetal liver (adult) stem cell derived erythroid cells

ERYTHROID PRODUCTION

RELATED APPLICATIONS

This application is a 35 U.S.C. §371 national stage application of PCT Application No. PCT/GB2013/051917, filed on Jul. 18, 2013, which claims priority from British Application No. 1212960.7, filed on Jul. 20, 2012, the contents of which are incorporated herein by reference in their entireties. The above-referenced PCT International Application was published as International Publication No. WO 2014/013255 A1 on Jan. 23, 2014.

FIELD OF THE INVENTION

This invention provides method and media suitable for inducing and supporting the differentiation of stem cells into erythroid cells.

BACKGROUND OF THE INVENTION

The production of red blood cells from stem cells (in particular human pluripotent stem cells (hPSC)) has been the subject of growing interest in the scientific community during recent years. This is in part, driven by the increased difficulty in obtaining sufficient clinically safe blood from donors to sustain global transfusion requirements.

Despite the increased interest in generating stem cell derived red blood cells there has been little progress made to take the early research discoveries towards the clinic and several major obstacles to RBC differentiation remain. Specifically, these are i) the efficiency of stem cell differentiation, ii) production of definitive as opposed to primitive erythroid cells, iii) sustained amplification throughout the differentiation process and iv) enucleation and terminal maturation of differentiated cells.

SUMMARY OF THE INVENTION

The present invention provides feeder-free culture systems and media to induce and support the differentiation of stem cells into erythroid cells.

In a first aspect, the invention provides a method of inducing differentiation of stem cells into erythroid cells, said method comprising the step of contacting stem cells with a GSK3 inhibitor and a phosphodiesterase inhibitor.

The GSK3 inhibitor may comprise a GSK3-beta (GSK3-β) inhibitor. The GSK3 inhibitor may comprise a specific GSK3 inhibitor; for example the GSK3 inhibitor may be comprise a specific GSK3-β inhibitor. One of skill will appreciate that a specific GSK3 inhibitor may bind to and/or inhibit GSK3 but may not detectably bind and/or inhibit any other kinase. The GSK3 inhibitor may comprise, for example, N-(4-methoxybenzyl)-N'-(5-nitro-1,3-thiazol-2-yl)urea—otherwise known as Inhibitor VIII or AR-A014418. The GSK3 inhibitor may be a N-(4-methoxybenzyl)-N'-(5-nitro-1,3-thiazol-2-yl) derivative or analogue. Additionally or alternatively, the GSK3 inhibitor may comprise CHIR99021 or a derivative or analogue thereof.

As such, references to GSK3 inhibitors in this specification should be understood as encompassing: (i) specific GSK3 inhibitors; (ii) GSK3-β inhibitors; (iii) Inhibitor VIII and/or (iv) CHIR99021

The phosphodiesterase inhibitor may be 3-isobutyl-1-methylxanthine (iso butyl methyl xanthine: (IBMX)). Compounds of this type may have the formula:

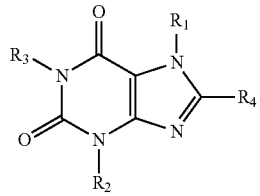

wherein $R_1$ is hydrogen, alkyl or methyl;
$R_2$ is hydrogen, alkyl, methyl or isobutyl;
$R_3$ is hydrogen, alkyl or methyl; and
$R_4$ is hydrogen, alkyl (lower or higher alkyl—for example linear or branched $C_1$-$C_6$ or $C_7$-$C_{10}$), phenyl, substituted phenyl, hydroxyl, methyl or $(CH_2)_n$—O—$R_5$,
wherein $R_5$ is hydrogen, alkyl or methyl.

This invention may exploit IBMX derivatives such as, for example, 8-MeO-IBMX—otherwise known as MMPX.

MMPX may have the formula:

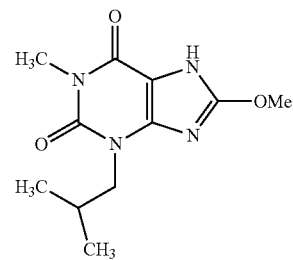

The methods provided by this invention may exploit Inhibitor VIII and/or CHIR99021 and IBMX.

The inventors have discovered that the methods described herein may be used to obtain improved yields of erythroid cells from stem cells. Specifically, the inventors have discovered that methods which comprise exposing or contacting cells with the GSK3 inhibitors and phosphodiesterase inhibitors described herein, result in the generation of erythroid cells exhibiting improved quality and which are near clinical grade. Additionally, erythroid cells produced by the methods described herein have been found to be more robust than those made by prior art methods. Additionally, it should be understood that the methods described herein may exploit suspension based liquid culture systems and are thus scalable. Moreover, the inventors have determined that the methods provided by this invention achieve a degree of efficiency high enough to avoid the need for any purification step (>80% HPC at d10 and >90% erythroid series by d24). In addition, the methods described herein support a considerable amplification of cell numbers as they differentiate to RBCs (up to about 350,000 fold d0-24)—this represents a considerable improvement over prior art methods, including those exploiting HoxB4 as an amplifying agent. The methods of this invention may be applied to human induced pluripotent stem cells (iPSC) or human embryonic stem cells—including (hESC) stem cell lines that have been derived under fully GMP compliant and licensed conditions. Cells of this type are generally referred to as "stem cells" in this specification (see the definition below). The inventors have further determined that stem cells subjected to the methods described herein reach the orthochromatic normoblast stage of erythropoiesis and display characteristics of definitive hematopoiesis (including the shut off of embryonic globins and expression of Aγ globin).

It should be understood that the term "stem cells" may be taken to refer to any cell which is able to self renew and indefinitely divide—cells of this type may be described as "immortal". In addition, when cultured under suitable conditions and/or contacted with, or exposed to, particular compounds and/or conditions, stem cells may differentiate into one or more of the specialised cell types which form embryonic and/or adult tissues.

Stem cells may be totipotent in nature and one of skill will appreciate that totipotent cells may be capable of generating a complete viable organism as well as any given specialised cell type. Stem cells may be pluripotent—cell of this type are not capable of generating a complete viable organism, but are able to differentiate to any specialised cell type. As such, the present invention may be applied to any type of totipotent and/or pluripotent stem cell.

The term "stem cells" may encompass embryonic, foetal, adult and/or induced pluripotent (iPS) stem cells. The term "stem cells" may further encompass progenitor cells of any type. In one embodiment, the stem cells mentioned herein may be mammalian cells; for example, the term "stem cells" may be applied to human and/or non-human stem cells of all types. By way of example this invention may relate to stem cells derived or obtained from, or provided by, primates, ungulates, ruminants and/or rodents (specifically, sheep, pigs, cattle, goats, horses, rats and mice).

Stem cells may be characterised by the presence of one or more markers selected from the group consisting of: ABCG2; ACE; ALCAM; Alkaline Phosphatase; beta-III Tubulin; BMP-2; BMPR-IA/ALK-3; BMPR-IB/ALK-6; BMPR-II; E-Cadherin; CCR4; CD9; CD71; CD90; CD90/Thy1; Cripto; CXCR4; DPPA5/ESG1; Endoglin/CD105; FABP1; FABP2; FGF-4; FGF R4; FoxD3; FoxP3; Frizzled-9; GAD1/GAD67; GATA-4; GATA-6; GDF-3; Glut1; HNF-3 beta; Integrin alpha 6/CD49f; Integrin beta 1/CD29; Lefty; MAP2; Musashi-1; Nanog; NCAM-L1; Nectin-2/CD112; Nestin; NeuroD1; Nodal; Noggin; NF-L; NF-M; Nucleostemin; Otx2; Oct ¾; PAX6; Podocalyxin; Prominin 2; ROBO3; Sca-I; SCF R/c-kit; SHH; SOX2; SOX7; SOX17; SPARC; SSEA-1; SSEA-3; SSEA-4; STAT3; STRO-1; TP63/TP73L; Tyrosine Hydroxylase; gamma-Secretase; alpha-Secretase; beta-Secretase; beta-III tubulin; alpha-Fetoprotein; beta-Catenin; Vimentin and VCAM-1. Collectively, these markers may each be referred to as stem cell markers and references in this specification to one or more "stem cell markers", may therefore encompass one or more of the abovementioned markers. One of skill will appreciate that to identify or detect a stem cell, a cell may be probed (using, for example antibodies or other agents capable of binding one or more of the listed stem cell markers) for the presence of one or more of the stem cell markers listed above.

It should be understood that the methods of this invention may be applied to any of the stem cells described above. A more detailed description of some specific types of stem cell is provided below.

This invention may be exploited to generate erythroid cells from embryonic stem cells (ESC), for example, mammalian and/or human embryonic stem cells (hESC). ESCs may be derived from early stage embryos and in particular from the inner cell mass of the developing morula or blastocyst. Embryonic stem cells, for example those derived from embryos in the stages immediately following conception (and for a short time thereafter), may be totipotent (capable of generating a complete viable organism as well as any given specialised cell type). Embryonic stem cells derived from later stage embryos (i.e. from the inner cell mass of a developing blastocyst) may be pluripotent (not capable of generating a complete viable organism, but capable of differentiating to any specialised cell type). As such, the present invention may be applied to embryonic (i.e. totipotent and/or pluripotent) stem cells.

One of skill will appreciate that hESCs and other cell lines for use in the methods described herein may be obtained from an embryo without destruction of the embryo, as described, for example, in Chung et al (Cell Stem Cell, vol 2, issue 2, 113-117, 2008). Stem cells may also be generated using the methods described by Chung et al., (2006) which methods involve taking a blastomere cell from an early stage embryo prior to formation of the blastocyst (at approximately the 8-cell stage) and co-culturing this cell with established stem cell lines to generate a fully competent stem cell line. Stem cells obtained by the methods described by Chung et al (2006, 2008) may be used to establish stem cell lines which them selves may serve as sources of stem cells for use in this invention.

Markers of embryonic stem cells may include, for example, ABCG2, Alkaline Phosphatase, E-Cadherin, CCR4, CD9, Cripto, DPPA5/ESG1, FGF-4, FGF R4, FoxD3, FoxP3, GDF-3, Integrin alpha 6/CD49f, Integrin beta 1/CD29, Lefty, Nanog, Oct ¾, Podocalyxin, SOX2, SPARC, SSEA-1, SSEA-3, SSEA-4 and STAT3.

The term "stem cells" may also be taken to refer to the pluripotent cells derived from any of the three primary germ layers (ectoderm, mesoderm and endoderm) which develop during the process of gastrulation. Cells derived from these layers may express one or more markers which may be used as a means of identification. By way of example, ectoderm germ layer may express markers, including, for example, Otx2, Nestin, TP63/TP73L, beta-III Tubulin, SHH, and PAX6. Ectoderm has the potential to form cell types such as neurons and early neuronal lineage markers include ACE, ALCAM, CD90/Thy1, GAD1/GAD67, Glut1, MAP2, NCAM-L1, Nectin-2/CD112, NeuroD1, NF-L, NF-M, ROBO3, gamma-Secretase, alpha-Secretase, beta-Secretase, beta-III tubulin, Tyrosine Hydroxylase. Neural stem cell markers include ABCG2, CXCR4, FGF R4, Frizzled-9, Musashi-1, Nestin, Noggin, Nucleostemin, Prominin 2, SOX2, Vimentin. Markers of early endodermal cells include, for example, FABP1, FABP2, GATA-4, HNF-3 beta (collectively referred to as definitive endodermal stem cells markers) as well as those markers for primitive endoderm such as alpha-Fetoprotein, beta-Catenin, GATA-4, SOX17 and SOX7.

The invention may also be applied to "adult" stem cells—cells of this type may be taken to be stem cells obtained from adult animals and or adult (or developed/differentiated) tissue (including adult humans and/or human (adult) tissue). However, it should be understood that the term "adult" also includes stem cells derived from neonatal, infant, juvenile and/or adolescent animals. Adult stem cells may be sourced from any suitable tissue, including bone marrow and/or specialised structures such as, for example hair follicles, skin, teeth and the like.

Stem cells to which this invention may be applied, may be obtained from a variety of sources including, for example, embryonic animals (including human embryos), said embryos being either aborted or created as part of a fertility program. Alternatively, it may be possible to obtain stem cells from established stem cell lines and thus avoiding the use of mammalian, particularly human, embryos. By way of example, stem cells for use in this invention may be obtained from the H1 and/or RC9/11/12/13 cell lines.

Alternatively, the methods of Meissner & Jaenisch (2006) may be used to obtain stem cells to which this invention may be applied. In these methods, the cdx2 gene is silenced in the donor nucleus during the process of nuclear transfer to prepare a reconstructed embryo from which a line of embryonic stem cells is derived. The cdx2 gene is turned back on in the isolated blastocyst cell taken from the embryo which is used to prepare the cell line. This is an example of, so-called, "alternative nuclear transfer" where the embryo is not capable of implantation but the stem cell line derived therefrom is fully competent.

The term "stem cells" may also encompass cells otherwise known as induced pluripotent stem cells (iPS). These are re-programmed adult somatic cells which have been modified to express certain factors (such as transcription regulators) and, as a consequence, become pluripotent and thus capable of differentiating to any other specialised cell type. As such, iPS cells, particularly mammalian, for example rodent iPS stem cells, may be cultured and/or maintained with the methods and/or compositions described herein.

An erythroid cell generated by the methods described may be characterised by expression of one or more haematopoietic/erythroid markers selected from the group consisting of: CD31; CD34; CD36; CD41a; CD43; CD45; CD71; and CD235a Stem cells to be used in the methods described herein may used directly from source. Additionally or alternatively, stem cells for use in this invention may comprise stem cells which have been maintained for a period of time.

Stem cells which are "maintained" may be retained in a proliferative and/or pluripotent state for a period or prolonged period of time and/or over a number of passages. Maintained stem cells may remain pluripotent or retain the pluripotent phenotype while at the same time being characterised by the expression of one or more of the stem cell markers described herein.

The stem cells for use in the methods described herein may be maintained by subjecting stem cells to a stem cell maintenance protocol. A stem cell maintenance protocol may comprise the use of media and/or substrates suitable for maintaining stem cells. For example, stem cells may be maintained in a stem cell medium such as, for example StemPro®. Additionally, the stem cells may be maintained on a substrate such as, for example, a CELLstart™ substrate. Maintained stem cells may be passaged every 1, 2, 3, 4, 5, 6, 7, 8, 9 or 10 days.

The methods described herein may include the additional step of inducing stem cells, for example stem cells which have been maintained for a period of time, to form embryoid bodies. One of skill will appreciate that stem cells may form embryoid bodies if subjected or exposed to specific conditions. By way of example, stem cells, for example those maintained using the maintenance protocols described herein, may be transferred to culture systems comprising low adherence substrates. When cultured on, or in the presence of, a low (for example ultra-low) adherence substrate, stem cells tend to form embryoid bodies. One of skill will appreciate that prior to being transferred to culture systems which induce the formation of embryoid bodies, confluent monolayers of stem cells may be cut or sectioned and clumps or sections of monolayer transferred to a culture system whereupon the sections and/or clumps may be induced to form embryoid bodies.

In view of the above, this invention may provide a method of inducing differentiation of stem cells (hESC) into erythroid cells, said method comprising the steps of:

(a) inducing stem cells to form embryoid bodies; and
(b) contacting the embryoid bodies with a GSK3 inhibitor and a phosphodiesterase inhibitor.

The method provided by the first aspect of this invention may comprise first and second phases. The first phase and second phases may comprise steps which progressively differentiate stem cells towards cells exhibiting characteristics of the mesodermal germ layer, cells of the haematopoietic lineage and ultimately erythroid cells.

The method may comprise a first phase (phase 1) in which stem cells or embryoid bodies are contacted with a GSK3 inhibitor (for example Inhibitor VIII and/or CHIR99021) and a second phase (phase 2) in which the cells are contacted with a phosphodiesterase inhibitor (such as IBMX). One of skill will appreciate that once contacted with a GSK3 inhibitor, stem cells may undergo a degree of differentiation (initially towards cells of the mesodermal germ layer specification and later towards cells of the haematopoietic lineage); as such, cells subjected to the second phase of the methods described herein may be referred to as partially differentiated stem cells or differentiated cells. One of skill will appreciate that the purpose of the second phase of the methods described herein is to differentiate cells produced by the first phase through haematopoietic lineages towards erythroid cells.

Phase 1 of the methods provided by this invention may comprise the step of contacting stem cells (or embryoid bodies formed therefrom) with a GSK3 inhibitor and one or more supplementary compounds. The supplementary compounds may be selected from the group consisting of:
(i) Bone Morphogenic Protein 4 (BMP4);
(ii) Vascular Endothelial Growth Factor 165 (VEGF);
(iii) Wnt3A and/or Wnt5a;
(iv) ActivinA;
(v) Fibroblast Growth Factor α (FGFα);
(vi) Stem Cell Factor (SCF); and
(vii) β-estradiol.

Phase 1 may comprise the step of contacting stem cells with culture media supplemented with a GSK3 inhibitor and one or more of the supplementary compounds noted above.

Phase 2 of the methods provided by this invention may comprise the step of contacting cells produced or generated by the phase one methods with a phosphodiesterase inhibitor and one or more supplementary compounds. The one or more supplementary compounds may be selected from the group consisting of:
(i) Bone Morphogenic Protein 4 (BMP4);
(ii) Vascular Endothelial Growth Factor 165 (VEGF);
(iii) Fibroblast Growth Factor α (FGFα);
(iv) Stem Cell Factor (SCF);
(v) β-estradiol.
(vi) Insulin-like Growth Factor 2 (IGF2);
(vii) Thrombopoietin (TPO);
(viii) Heparin;
(ix) Hydrocortisone;
(x) Flt3-Ligand;
(xi) Interleukin 3 (IL3);
(xii) IL11;
(xii) Erythropoietin (EPO);
(xiv) Insulin Growth Factor 1 (IGF1);
(xv) StemRegenin1 (SR); and
(xvi) Pluripotin (SC1)

Phase 2 may comprise the step of contacting stem cells with culture media supplemented with a phosphodiesterase inhibitor and one or more of the supplementary compounds noted above.

The latter stages of phase 2 may exploit methods in which stem cells or cells differentiated therefrom, are contacted with media supplemented with EPO alone.

Phase 1 of the methods described herein may comprise a first sub phase (referred to herein after as "sub-phase 1a"). Sub-phase 1a may comprise the step of contacting stem cells (or embryoid bodies) with one or more compounds selected from the group consisting of:
(i) a GSK3 inhibitor;
(ii) Bone Morphogenic Protein 4 (BMP4);
(iii) Vascular Endothelial Growth Factor 165 (VEGF);
(iv) Wnt3A and/or Wnt5A; and
(v) ActivinA.

Phase 1 of the methods described herein may further comprise a second sub-phase (referred to hereinafter as "sub-phase 1b") executed after sub-phase 1a. Sub-phase 1b may comprise the step of contacting the stem cells (or embryoid bodies) with one or more compounds selected from the group consisting of:
(i) a GSK3 inhibitor;
(ii) Bone Morphogenic Protein 4 (BMP4);
(iii) Vascular Endothelial Growth Factor 165 (VEGF);
(iv) Wnt3A and/or Wnt5A;
(v) ActivinA;
(vi) Fibroblast Growth Factor α (FGFα);
(vii) Stem Cell Factor (SCF); and
(viii) β-estradiol.

Optionally and before execution of phase 2 of the methods described herein, cells or embryoid bodies provided or produced by phase 1 (and in particular sub-phases 1a and 1b) of the method may be subjected to a dissociation protocol. For example, cells or embryoid bodies provided or produced by phase 1 of the method may be mechanically or chemically dissociated, and harvested by, for example centrifugation. Harvested cells may (after re-suspension) be subjected to phase 2. Harvested cells may be re-suspended in suitable medium such as, for example, Stemline II. Additionally, and prior to execution of phase 2, cells may be plated out at around $200 \times 10^3$ cells/per well.

Phase 2 of the methods described here may comprise a first sub phase (referred to hereinafter sub-phase 2a). Sub-phase 2a may comprise the step of contacting the cells or embryoid bodies provided or produced by the first phase (and specifically sub-phases 1a and 1b), which cells or embryoid bodies may have been subjected to dissociation and harvesting protocols, with one or more compounds selected from the group consisting of:
(i) BMP4;
(ii) VEGF;
(iii) FGFα;
(iv) SCF;
(v) Insulin-like Growth Factor 2 (IGF2);
(vi) Thrombopoietin (TPO);
(vii) Heparin;
(viii) A phosphodiesterase inhibitor (for example IBMX); and
(ix) β-estradiol.

Phase 2 may further comprise a second sub-phase (referred to hereinafter as "sub-phase 2b"). Sub-phase 2b may comprise repeating the method of sub-phase 2a—in other words, sub-phase 2b comprises the step of contacting cells subjected to sub-phase 2a with one or more of the compounds listed as (i)-(ix) immediately above. Optionally, the cytokines used in sub-phase 2b (compounds (i)-(ix) listed immediately above) may be supplemented with a quantity of StemRegenin1 (SR1). The inventors have discovered that the optional addition of SR1 during sub-phase 2b (at day 5) enhances or increases the rate of cell amplification—in particular in later stages of the protocols of this invention. Moreover, the inventors noted that cells cultured using methods which exploit StemRegenin1 (SR1) are more "sturdy" and less prone to lysis.

Phase 2 of the methods described herein may further comprise a third sub-phase (referred to hereinafter as "sub-phase 2c"). Sub-phase 2c may replicate the method of sub-phase 2a and/or 2b. Optionally, before executing sub-phase 2c, the cells produced by sub-phase 2b may first be harvested by, for example centrifugation. Moreover, if the total number of cells after sub-phase 2b exceeds $500 \times 10^3$, the cells may be split before executing sub-phase 2c. Additionally, throughout sub-phase 2c, the total cell number may be kept under $1 \times 10^6$ per ml.

Phase 2 of the methods described herein may comprise a fourth sub-phase (referred to herein after as sub-phase 2d). Sub-phase 2d may replicate the method of sub-phase 2a. Sub-phase 2d comprises the step of contacting cells provided or produced by sub-phase 2c with one or more of the compounds selected from the group consisting of:
(i) BMP4;
(ii) VEGF;
(iii) FGFα;
(iv) SCF;
(v) Insulin-like Growth Factor 2 (IGF2);
(vi) Thrombopoietin (TPO);
(vii) Heparin;
(viii) A phosphodiesterase inhibitor (for example IBMX); and
(ix) β-estradiol.

The concentration of the one or more compounds used in sub-phase 2d may be half that used in sub-phase 2a.

Phase 2 of the methods described herein may comprise a fifth sub-phase (referred to herein after as "sub-phase 2e"). Sub-phase 2e may comprise the step of contacting cells produced or provided by sub-phase 2d, with one or more compounds selected from the group consisting of:
(i) Hydrocortisone;
(ii) SCF;
(iii) Flt3-Ligand;
(iv) BMP4;
(v) Interleukin 3 (IL3);
(vi) IL11;
(vii) A phosphodiesterase inhibitor (for example IBMX); and
(viii) Erythropoietin (EPO).

Optionally, sub-phase 2e may be repeated 1, 2, 3, 4, 5, 6, 7, 8, 9 or 10 times and the time between each repeat of sub-phase 2e may be 1, 2 or 3 days. Preferably, sub-phase 2e may be repeated 3 or 5 times with the time between each repeat being approximately 2 days.

During sub-phase 2e, the cells may be further or additionally contacted with a quantity of pluripotin (SC1). For example on about day 14 and about day 16, the cells may be contacted with pluripotin (SC1). Again, the inventors have discovered that the optional addition of pluripotin (SC1) during sub-phase 2e (at about, for example day 14 or 16) enhances or increases the rate of cell amplification in later stages of the protocols of this invention. Moreover, the inventors noted that cells cultured using methods involving the use of pluripotin (SC1) were more "sturdy" and less prone lysis.

Phase 2 of this invention may comprise a sixth sub-phase (referred to hereinafter as "sub-phase 2f"). Sub-phase 2f may comprise the step of contacting the cells produced or provided by sub-phase 2f with one or more compounds selected from the group consisting of:
(i) Hydrocortisone;
(ii) SCF;
(iii) Insulin Growth Factor 1 (IGF1);
(iv) IL3;
(v) IL11; and
(vi) EPO.

Prior to executing sub-phase 2f, cells provide or produced by sub-phase 2e may be transferred to IBIT medium. One of skill will appreciate that IBIT medium may comprise, for example, Incomplete Iscove's Medium supplemented with stable glutamine, Albumin (for example human and/or (foetal) bovine serum albumin), Insulin, Transferrin and xeno-free component lipid mixture solution. Sub-phase 2f, may comprise the stem of using IBIT medium supplemented with the cytokines listed as (i) to (vi) above. Optionally and prior to executing sub-phase 2f, cells provided or produced by sub-phase 2e may be harvested (perhaps by centrifugation) and plated out at a density of between about $500\times10^3$ to about $1\times10^6$ per 3 ml of IBIT medium.

Sub-phase 2f may be repeated 1, 2, 3 or 4 times. Moreover, each time sub-phase 2f is repeated, fresh IBIT medium and fresh compounds may be used.

Phase 2 of the methods described herein may comprise a seventh sub-phase (referred to hereinafter as "sub-phase 2g"). Sub-phase 2g may comprise the step of harvesting (perhaps by centrifugation) cells produced or generated by sub-phase 2f. Sub-phase 2g may further comprise the step of maintaining (optionally harvested) cells generated or produced by sub-phase 2f in IBIT medium supplemented with EPO. Optionally harvested cells produced or generated by sub-phase 2f may be maintained in IBIT supplemented with EPO for about 1, 1.5, 2, 2.5 or 3 days. Sub-phase 2g may comprise the further step of, after maintaining cells in IBIT supplemented with EPO, maintaining the cells in IBIT alone. Cells may be maintained in IBIT medium for about 3, 4, 4.5, 5, 5.5, 6, 7, 8, 9, 9.5, 10, 10.5, 11, 12, 13 or 14 days.

The present invention provides a method of inducing differentiation of stem cells into erythroid cells, said method comprising executing phase 1 as described herein and then phase 2 as described herein, wherein phase 1 comprises sub-phases 1a and 1b and phase 2 comprises sub-phases 2a-2g.

The present invention provides a method of inducing differentiation of stem cells into erythroid cells, said method comprising the steps of:
(a) maintaining stem cells and inducing the formation of embryoid bodies;
(b) subjecting the embryoid bodies to the sub-phase 1a;
(c) subjecting the product of sub-phase 1a to sub-phase 1b;
(d) subjecting the product of sub-phase 1b to sub-phase 2a;
(e) subjecting the product of sub-phase 2a to sub-phase 2b;
(f) subjecting the product of sub-phase 2b to sub-phase 2c;
(g) subjecting the product of sub-phase 2c to sub-phase 2d;
(h) subjecting the product of sub-phase 2e to sub-phase 2f; and
(i) subjecting the product of sub-phase 2f to sub-phase 2g; wherein the product of sub-phase 2g is an erythroid cell.

The methods provided by this invention may be executed over a number of days. Sub-phase 1a may represent the first step of the methods described herein; as such, sub-phase 1a may be executed on day 0. Sub-phase 1a may last about 1, 2 or 3 days. Sub-phase 1a may last about 2 days.

Sub-phase 1b may last about 0.5, 1 or 2 days. Sub-phase 1b may last about 1 day.

Sub-phase 2a may last about 1, 2 or 3 days. Sub-phase 2a may last about 2 days.

Sub-phase 2b may last about 1, 2 or 3 days. Sub-phase 2b may last about 2 days.

Sub-phase 2c may last about 1, 2 or 3 days. Sub-phase 2c may last about 2 days.

Sub-phase 2d may last about 0.5, 1, 1.5 or 2 days. Sub-phase 2d may last about 1 day.

Sub-phase 2e may last about 4, 5, 6, 6.5, 7, 7.5, 8, 9, 10, 10.5, 11, 11.5, 12, 13, or 14 days. Sub-phase 2e may last about 7 days or about 11 days Sub-phase 2f may last about 5, 6, 6.5, 7, 7.5 or 8 days. Sub-phase 2f may last about 7 days.

Sub-phase 2g may last about 3, 4, 5, 6, 6.5, 7, 7.5, 8, 9, 10, 11, 11.5, 12, 12.5, 13, 14, 15, 16, 17, 18, 19, 20 or 21 days. Sub-phase 2g may last about 7 or about 12 days.

As stated, sub-phase 1a may represent the first step of the methods described herein; as such, sub-phase 1a may be executed on day 0 and sub-phase 1b may be executed on about day 2. Sub-phase 2a may be executed on about day 3 and sub-phase 2b may be executed on about day 5. Sub-phase 2c may be executed on day 7 and sub-phase 2d may be executed on about day 9. Sub-phase 2e may be executed on about day 10 and sub-phase 2f may be executed on about day 17 or on about day 21. Sub-phase 2g may be executed on about day 24 or on about day 28.

GSK3 inhibitors for use in this invention may be used at final concentrations of about 0.05, 0.1, 0.2, 0.3, 0.4, 0.5, 1, 1.5, 2, 2.5, 3, 4 or 5 µM. For example, Inhibitor VIII may be used at a final concentration of about 2 µM in both sub-phases 1a and 1b of the methods described herein. CHIR99021 may be used at a final concentration of about 0.2 µM in sub-phases 1a and 1b of the methods outlined above.

Bone Morphogenic Protein 4 (BMP4) may be used at a final concentration of about 1, 5, 10, 15, 20 or 25 ng/ml. For example, in sub-phase 1a, BMP-4 may be used at a final concentration of about 5, 6, 7, 8, 9, 10, 11, 12, 13, 14 or 15 ng/ml. In sub-phase 1a, BMP4 may be used at a final concentration of about 10 ng/ml. In sub-phases 1b and 2a, 2b and 2c, BMP 4 may be used at a final concentration of about 15, 17.5, 20, 22.5 or 25 ng/ml. In sub-phases 1b, 2a, 2b and 2c, BMP-4 may be used at a final concentration of about 20 ng/ml. In sub-phase 2d, BMP4 may be used at a final concentration of about 5, 7, 10, 12 or 15 ng/ml. In sub-phase 2d, BMP4 may be used at a final concentration of about 10 ng/ml. In sub-phase 2e, BMP4 may be used at a final concentration of about 6, 6.2, 6.4, 6.5, 6.6, 6.7, 6.8, 7 or 7.5 ng/ml. In sub-phase 2e, BMP4 may be used at a final concentration of about 6.7 ng/ml.

VEGF may be used at a final concentration of about 5, 10, 12.5, 15, 17.5, 20, 25, 30 or 35 ng/ml. In subphases 1a and 1b, VEGF may be used at a final concentration of about 10 ng/ml whereas in sub-phase 2a, VEGF may be used at a final concentration of about 30 ng/ml. In sub-phase 2d, VEGF may be used at a final concentration of about 15 ng/ml.

Wnt3A and/or Wnt5A may be used at a final concentration of about 5, 7.5, 10, 12.5 or 15 ng/ml. In sub-phases 1a and 1b, Wnt3A and/or Wnt5A may be used at a final concentration of about 10 ng/ml.

Activin A may be used at a final concentration of about 1, 2, 3, 4, 5, 6, 7, 8, 9 or 10 ng/ml. In sub-phases 1a and 1b, ActivinA may be used at a final concentration of about 5 ng/ml.

FGFα may be used at a final concentration of about 5, 7.5, 10, 12.5 or 15 ng/ml. In sub-phases 1b, 2a, 2b and 2c FGFα may be used at a final concentration of about 10 ng/ml. In sub-phase 2d, FGFα may be used at a final concentration of about 5 ng/ml.

SCF may be used at a final concentration of about 10, 14.5, 15, 15.5, 19.5, 20, 20.5 25, 29.5, 30 and 30.5 ng/ml. In sub-phases 2a, 2b and 2c, SCF may be used at a final concentration of about 30 ng/ml. In sub-phase 2d, SCF may be used at a final concentration of about 15 ng/ml. In sub-phase 2f, SCF may be used at a final concentration of about 20 ng/ml.

IGF2 may be used at a final concentration of about 1, 2, 3, 4, 4.5, 5, 5.5, 7.5, 10, 12.5 or 15 ng/ml. In sub-phases, 2a, 2b and 2c, IGF2 may be used at a final concentration of about 10 ng/ml. In sub-phase 2d, IGF2 may be used at a final concentration of about 5 ng/ml.

TPO may be used at a final concentration of about 1, 2, 3, 4, 4.5, 5, 5.5, 7.5, 10, 12.5 or 15 ng/ml. In sub-phases, 2a, 2b and 2c, TPO may be used at a final concentration of about 10 ng/ml. In sub-phase 2d, TPO may be used at a final concentration of about 5 ng/ml.

Heparin may be used at a final concentration of about 1, 1.5, 2, 2.5, 3, 3.5 4, 4.5 or 5 ng/ml. In sub-phases, 2a, 2b and 2c, Heparin may be used at a final concentration of about 5 ng/ml. In sub-phase 2d, Heparin may be used at a final concentration of about 2.5 ng/ml.

The phosphodiesterase inhibitor (for example IBMX) may be used at a final concentration of about 10, 20, 23, 24, 25, 26, 27, 30, 40, 45, 50, 55, 60, 70, 80, 90 or 100 µM. In sub-phases, 2a, 2b, 2c and 2e the phosphodiesterase inhibitor (for example IBMX) may be used at a final concentration of about 50 µM. In sub-phase 2d, the phosphodiesterase inhibitor (for example IBMX) may be used at a final concentration of about 25 µM.

β-estradiol may be used at a final concentration of about 0.1, 0.15, 0.2, 0.25, 0.3, 0.35, 0.4, 0.45, 0.5, 0.6, 0.7, 0.8, 0.9 or 1 ng/ml. In sub-phases, 1b, 2a, 2b and 2c 3-estradiol may be used at a final concentration of about 0.4 ng/ml. In sub-phase 2d, 3-estradiol may be used at a final concentration of about 0.2 ng/ml.

Hydrocortisone may be used at a final concentration of about $0.1 \times 10^{-6}$M, $0.2 \times 10^{-6}$M, $0.5 \times 10^{-6}$M, $1 \times 10^{-6}$M, $2 \times 10^{-6}$M, $3 \times 10^{-6}$M, $4 \times 10^{-6}$M, $5 \times 10^{-6}$M, $6 \times 10^{-6}$M, $7 \times 10^{-6}$M, $8 \times 10^{-6}$M, $9 \times 10^{-6}$M or $10 \times 10^{-6}$. Hydrocortisone may be used at a concentration of about $1 \times 10^{-6}$M.

Flt3 ligand may be used at a final concentration of about 30, 40, 45, 50, 55 ng/ml. In sub-phase, 2e, Flt3 ligand may be used at a final concentration of about 50 ng/ml.

IL3 may be used at a final concentration of about 6, 6.2, 6.4, 6.5, 6.6, 6.7, 6.8, 7 or 7.5 ng/ml. In sub-phase 2e and 2f, IL3 may be used at a final concentration of about 6.7 ng/ml.

IL11 may be used at a final concentration of about 6, 6.2, 6.4, 6.5, 6.6, 6.7, 6.8, 7 or 7.5 ng/ml. In sub-phase 2e and 2f, IL11 may be used at a final concentration of about 6.7 ng/ml.

IGF1 may be used at a final concentration of about 5, 10, 15, 20, 25 or 30 ng/ml. In sub-phase 2f, IGF1 may be used at a final concentration of about 20 ng/ml.

EPO may be used at a final concentration of about 1, 1.5, 2, 2.5, 3, 3.5, 4, 4.5 or 5 U/ml. In sub-phase 2f, EPO may be used at a final concentration of about 2 U/ml. In sub-phase 2g, EPO may be used at a final concentration of about 4 U/ml.

StemRegenin1 (SR1) may be used at a final concentration of about 0.1-10 µM. For example a final concentration of 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5 or 10 µM may be used in sub-phase 2b. Typically, a final concentration of about 1 µM StemRegenin (SR1) is used.

Pluripotin (SC1) may be used at a final concentration of about 100-1000 nM. 0.1-10 µM. For example a final concentration of 100, 150, 200, 250, 300, 350, 400, 450, 500, 550, 600, 650, 700, 750, 800, 850, 900, 950 or 1000 nM may be used in sub-phase 2e. Typically, a final concentration of about 250 nM or about 500 nM Pluripotin (SC1) is used. For example, on about day 14 of sub-phase 2e, about 500 nM Pluripotin (SC1) may be added. On about day 16, about 250 nM Pluripotin maybe added.

It should be understood that the concentrations and amounts of the various supplementary compounds indicated above, may be the final concentrations/amounts of each compound in a culture medium. Some suitable forms of culture media for use in the methods described herein discussed in more detail below, however any of sub-phases 1a, 1b, 2a, 2b, 2c, 2d and 2e described above may utilise any base culture media suitable for the maintenance and/or expansion/differentiation of stem cells. For example, these sub-phases may exploit volumes of an Iscove's Modified Dulbecco's Media (IMDM) or Dulbecco's Modified Eagle Medium based medium. Media of this type include, for example, one or more selected from the group consisting of:
  (i) Stemline® I and II (Sigma)
  (ii) Stemspan® (Stem Cell Technologies)
  (iii) X-vivo 10, 15 or 20 (BioWhittaker/Lonza)
  (iv) StemPro® 34 (Life Technologies)
  (v) Poietics HPGM (Lonza)
  (vi) APEL (Stem Cell Technologies)
  (vii) Other custom or "home made" medium based on IMDM or DMEM+ factors (similar to BIT).

It should be understood that the various final concentrations and amounts of the supplementary compounds described herein may be the final concentrations and amounts of the supplementary compounds added to the base media.

The present invention further provides media for use in the methods described herein and a second aspect, the invention provides a medium for inducing differentiation of stem cells into erythroid cells and/or for use in a method of inducing differentiation of stem cells into erythroid cells, said medium comprising a GSK3 inhibitor and/or a phosphodiesterase inhibitor and one or more supplementary compounds selected from the group consisting of:
  (i) Bone Morphogenic Protein 4 (BMP4);
  (ii) Vascular Endothelial Growth Factor 165 (VEGF);
  (iii) Wnt3A and/or Wnt5A;
  (iv) ActivinA.
  (v) Fibroblast Growth Factor α (FGFα);
  (vi) Stem Cell Factor (SCF);
  (vii) β-estradiol.
  (viii) Insulin-like Growth Factor 2 (IGF2);
  (ix) Thrombopoietin (TPO);
  (x) Heparin;
  (xi) Hydrocortisone;
  (xii) Flt3-Ligand;
  (xiii) Interleukin 3 (IL3);
  (xiv) IL11;
  (xv) Erythropoietin (EPO);
  (xvi) Insulin Growth Factor 1 (IGF1);
  (xvii) StemRegenin1 (SR1); and
  (xviii) Pluripotin (SC1)

The medium provided by this invention may comprise a base medium suitable for the maintenance and/or expansion of stem cells. The base medium may comprise a medium suitable for the maintenance and/or expansion of stem cells. Media of this type may comprise, for example, compounds and molecules which facilitate the maintenance and/or expansion of stem cells. The base medium may comprise an Iscove's Modified Dulbecco's Media (IMDM) or Dulbecco's Modified Eagle Medium based medium. By way of example, the base medium may comprise one or more selected from the group consisting of:
 (i) Stemline® I and II (Sigma)
 (ii) Stemspan® (Stem Cell Technologies)
 (iii) X-vivo 10, 15 and 20 (BioWhittaker/Lonza)
 (iv) StemPro® 34 (Life Technologies)
 (v) Poietics HPGM (Lonza)
 (vi) APEL (Stem Cell Technologies)
 (vii) Other custom or "home made" medium based on IMDM or DMEM+ factors (similar to BIT).

Suitable base media may be serum free.

The base medium may comprise, for example, Stemline® II medium (Sigma-Aldrich Co. LLP).

The methods described herein may utilise any IMDM or DMEM based media but by way of example, the methods may utilise media comprising Stemline® II. Media of this type may be suitable for use in any of sub-phases 1a, 1b, 2a, 2b, 2c, 2d and/or 2e.

Where the methods require the maintenance or expansion of erythrocyte precursor cells—such as might occur in sub-phases 2f and/or 2g, the base medium may comprise IBIT medium itself comprises Incomplete Iscove's medium supplemented with stable glutamine, bovine serum albumin, insulin, transferring and xeno-free component lipid mixture solution.

A medium for inducing differentiation of stem cells into erythroid cells and/or for use in a method of inducing differentiation of stem cells into erythroid cells may comprise a GSK3 inhibitor and one or more compounds selected from the group consisting of:
 (i) Bone Morphogenic Protein 4 (BMP4);
 (ii) Vascular Endothelial Growth Factor 165 (VEGF);
 (iii) Wnt3A and/or Wnt5A;
 (iv) ActivinA.
 (v) Fibroblast Growth Factor α (FGFα);
 (vi) Stem Cell Factor (SCF);
 (vii) β-estradiol.
 (viii) Insulin-like Growth Factor 2 (IGF2);
 (ix) Thrombopoietin (TPO);
 (x) Heparin;
 (xi) Hydrocortisone;
 (xii) Flt3-Ligand;
 (xiii) Interleukin 3 (IL3);
 (xiv) IL11;
 (xv) Erythropoietin (EPO); and
 (xvi) Insulin Growth Factor 1 (IGF1).

A medium for inducing differentiation of stem cells into erythroid cells and/or for use in a method of inducing differentiation of stem cells into erythroid cells may comprise:
 (i) a GSK3 inhibitor
 (ii) Bone Morphogenic Protein 4 (BMP4);
 (iii) Vascular Endothelial Growth Factor 165 (VEGF);
 (iv) Wnt3A and/or Wnt5A;
 (v) ActivinA.
 (vi) Fibroblast Growth Factor α (FGFα);
 (vii) Stem Cell Factor (SCF); and
 (viii) β-estradiol.

A medium for inducing differentiation of stem cells into erythroid cells and/or for use in a method of inducing differentiation of stem cells into erythroid cells may comprise:
 (i) a GSK3 inhibitor
 (ii) Bone Morphogenic Protein 4 (BMP4);
 (iii) Vascular Endothelial Growth Factor 165 (VEGF);
 (iv) Wnt3A and/or Wnt5A; and
 (v) ActivinA.

A medium of the type described immediately above may be used in sub-phase 1a of the methods described herein.

A medium for inducing differentiation of stem cells into erythroid cells and/or for use in a method of inducing differentiation of stem cells into erythroid cells may comprise:
 (i) a GSK3 inhibitor
 (ii) Bone Morphogenic Protein 4 (BMP4);
 (iii) Vascular Endothelial Growth Factor 165 (VEGF);
 (iv) Wnt3A and/or Wnt5A;
 (v) ActivinA.
 (vi) Fibroblast Growth Factor α (FGFα);
 (vii) Stem Cell Factor (SCF); and
 (viii) β-estradiol.

A medium of the type described immediately above may be used in sub-phase 1b of the methods described herein.

A medium for inducing differentiation of stem cells into erythroid cells and/or for use in a method of inducing differentiation of stem cells into erythroid cells may comprise one or more compounds selected from the group:
 (i) A phosphodiesterase inhibitor;
 (ii) Bone Morphogenic Protein 4 (BMP4);
 (iii) Vascular Endothelial Growth Factor 165 (VEGF);
 (iv) Fibroblast Growth Factor α (FGFα);
 (v) Stem Cell Factor (SCF);
 (vi) Insulin-like Growth Factor 2 (IGF2);
 (vii) Thrombopoietin (TPO);
 (viii) Heparin;
 (ix) β-estradiol
 (x) Hydrocortisone;
 (xi) Flt3-Ligand;
 (xii) Interleukin 3 (IL3);
 (xiii) IL11;
 (xiv) Erythropoietin (EPO);
 (xv) StemRegenin1 (SR1); and
 (xvi) Pluripotin (SC1)

A medium for inducing differentiation of stem cells into erythroid cells and/or for use in a method of inducing differentiation of stem cells into erythroid cells may comprise
 (i) A phosphodiesterase inhibitor;
 (ii) Bone Morphogenic Protein 4 (BMP4);
 (iii) Vascular Endothelial Growth Factor 165 (VEGF);
 (iv) Fibroblast Growth Factor α (FGFα);
 (v) Stem Cell Factor (SCF);
 (vi) Insulin-like Growth Factor 2 (IGF2);
 (vii) Thrombopoietin (TPO);
 (viii) Heparin; and
 (ix) β-estradiol A medium of the type described immediately above may be used in sub-phases 2a, 2b, 2c and 2d of the methods described herein.

A medium for inducing differentiation of stem cells into erythroid cells and/or for use in a method of inducing differentiation of stem cells into erythroid cells may comprise:
 (i) A phosphodiesterase inhibitor
 (ii) Bone Morphogenic Protein 4 (BMP4);

(iii) Hydrocortisone;
(iv) Flt3-Ligand;
(v) Interleukin 3 (IL3);
(vi) IL11;
(vii) Erythropoietin (EPO);
(viii) StemRegenin1 (SR1); and
(ix) Pluripotin (SC1)

A medium of the type described immediately above may be used in sub-phase 2e of the methods described herein.

The media described above and which are suitable for use in sub-phases 1a, 1b, 2a, 2b, 2c, 2d and 2e of the methods provided by this invention may further comprise Stemline® II.

A medium for inducing differentiation of stem cells into erythroid cells and/or for use in a method of inducing differentiation of stem cells into erythroid cells may comprise:
(i) Stem Cell Factor (SCF);
(ii) Hydrocortisone;
(iii) Interleukin 3 (IL3);
(iv) IL11;
(v) Erythropoietin (EPO); and
(vi) Insulin Growth Factor 1 (IGF1).

A medium of the type described immediately above may be used in sub-phase 2f of the methods described herein.

A medium for inducing differentiation of stem cells into erythroid cells and/or for use in a method of inducing differentiation of stem cells into erythroid cells may comprise Erythropoietin (EPO).

A medium of the type described immediately above may be used in sub-phase 2g of the methods described herein.

Media suitable for use in sub-phases 2f and 2g (such as the media described above) may further comprise IBIT medium as defined above.

It should be understood that the precise concentrations and amounts of various supplementary compounds described above may vary depending upon the application but in general, the media provided by this invention may contain concentrations and amounts of supplementary compounds substantially identical or similar to the concentration and amounts required in the methods described herein. Suitable concentrations and amounts of the various supplementary compounds are described in more detail above (see section discussing methods and sub-phases).

In a third aspect, the present invention provides a kit for inducing differentiation of stem cells into erythroid cells and/or for use in a method of inducing differentiation of stem cells into erythroid cells, said kit comprising one or more components selected from the group consisting of:
(a) one or more of the media described herein;
(b) one or more compounds selected from the group consisting of:
(i) Bone Morphogenic Protein 4 (BMP4);
(ii) Vascular Endothelial Growth Factor 165 (VEGF);
(iii) Wnt3A and/or Wnt5A;
(iv) ActivinA.
(v) Fibroblast Growth Factor α (FGFα);
(vi) Stem Cell Factor (SCF);
(vii) β-estradiol.
(viii) Insulin-like Growth Factor 2 (IGF2);
(ix) Thrombopoietin (TPO);
(x) Heparin;
(xi) Hydrocortisone;
(xii) Flt3-Ligand;
(xiii) Interleukin 3 (IL3);
(xiv) IL11;
(xv) Erythropoietin (EPO);
(xvi) Insulin Growth Factor 1 (IGF1).
(xvii) StemRegenin1 (SR1); and
(xviii) Pluripotin (SC1)
(c) Optionally sterile receptacles for the culture and/or maintenance of stem cells, embryoid bodies and/or cells;
(d) Tools and/or implements for adding supplements to media (for example pipettes and/or syringes); and
(e) Instructions for use.

In a fourth aspect, the present invention provides an erythroid cell produced or obtainable by the methods described herein.

In a fifth aspect, the present invention provides methods and media as described above and in the detailed description and figures which follow.

DETAILED DESCRIPTION

The present invention will now be described in detail with reference to the following figures which show:

FIG. 1: Adherent culture (d3-10) is not required for expansion & differentiation. Histogram representative of total fold amplification of erythroid differentiation culture of hESC line H1 cultivated in the presence of Inhibitor VIII on normal tissue culture treated surface or on ultra low adherence surface between day 3 and day 10.

Figure 2:
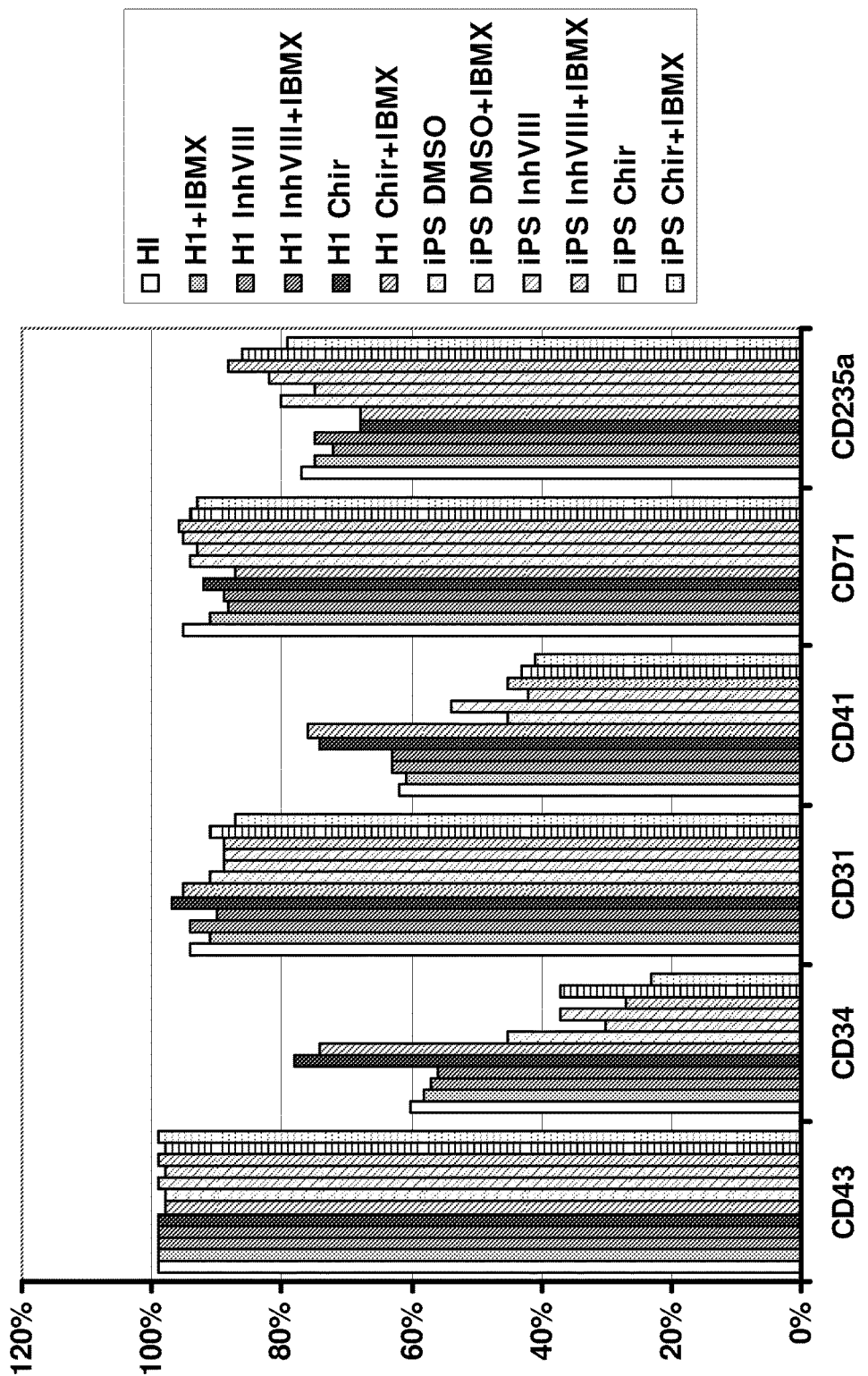

FIG. 2: Effect of GSK inhibitor on phenotype at d10. Flow cytometry analysis of differentiating hPSCs at day 10 of erythroid culture. All the cells tested show a high positivity for the pan hematopoietic CD43 antigen. The presence of CD34, CD31, CD41 and CD235a indicate that the analyzed cells are either at an hemangioblastic or shortly post hemangioblastic stage. The differences observed between H1 and iPSC reflect the differential kinetics of differentiation intrinsic to these cell lines.

Figure 3A:
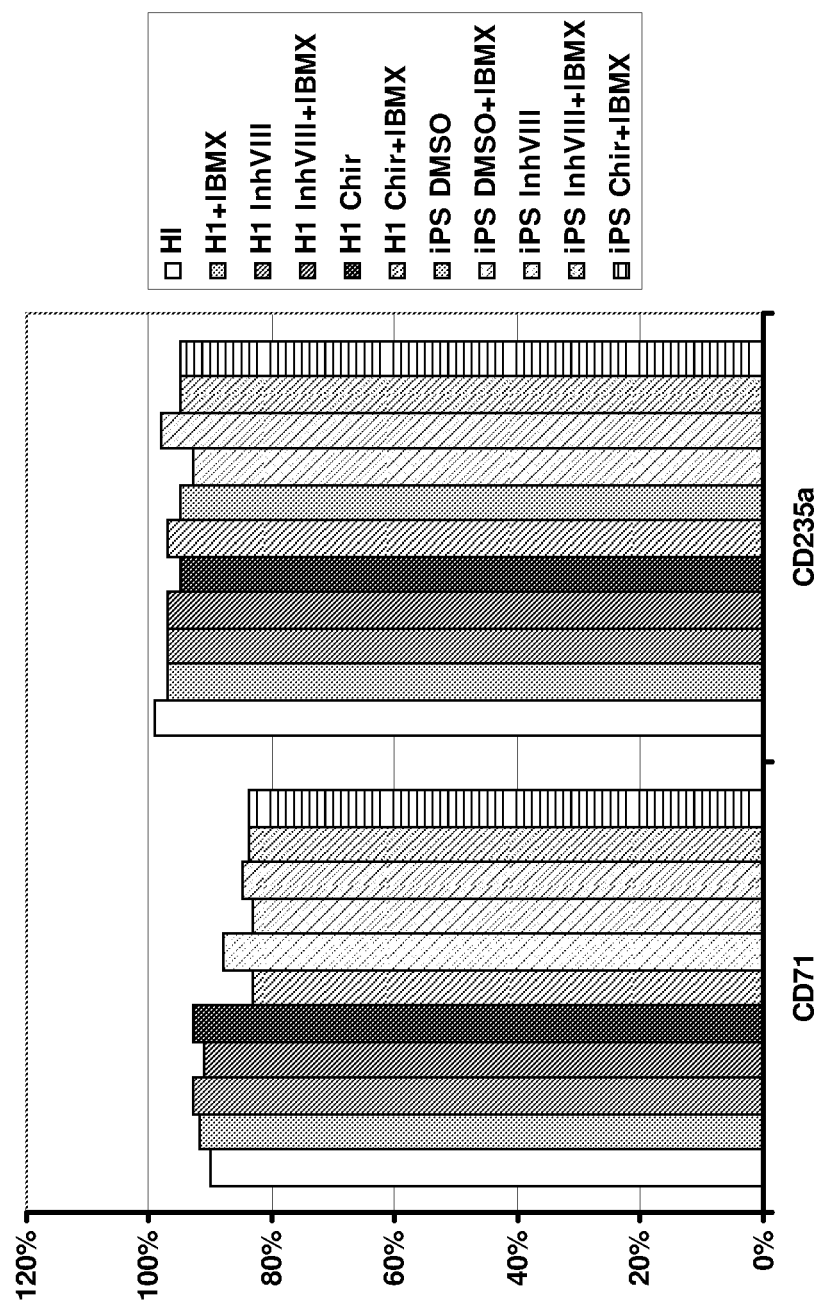
Figure 3B:
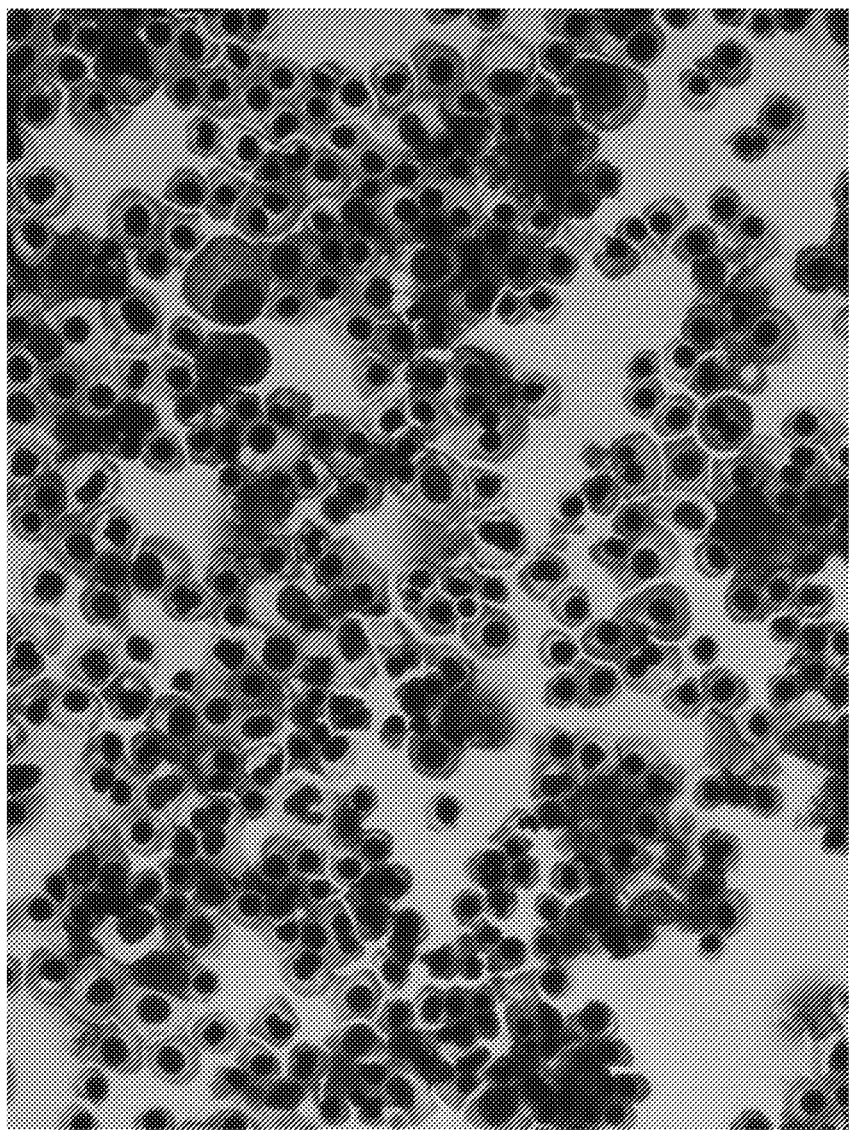

FIGS. 3A and 3B: >90% CD235a (GlyA+) erythroid cells at d24. FIG. 3A. Flow cytometry analysis of differentiated hPSCs at day 28 in erythroid culture conditions. The presence of transferring receptor (CD71) on more of 80% of the cells analysed show that the cells are still in expansion phase and the presence of glycophorin A (CD235a) on more than 95% of the cells analysed while CD31, CD34 and CD41 have disappeared (data not shown) is a good indicator of the erythroid character of the cells. FIG. 3B. Rapid Romanovski staining of a cytospin preparation of hiPSC differentiated into erythroid cells at day 28, the cells are mainly orthochromatic normoblasts.

Figure 4:
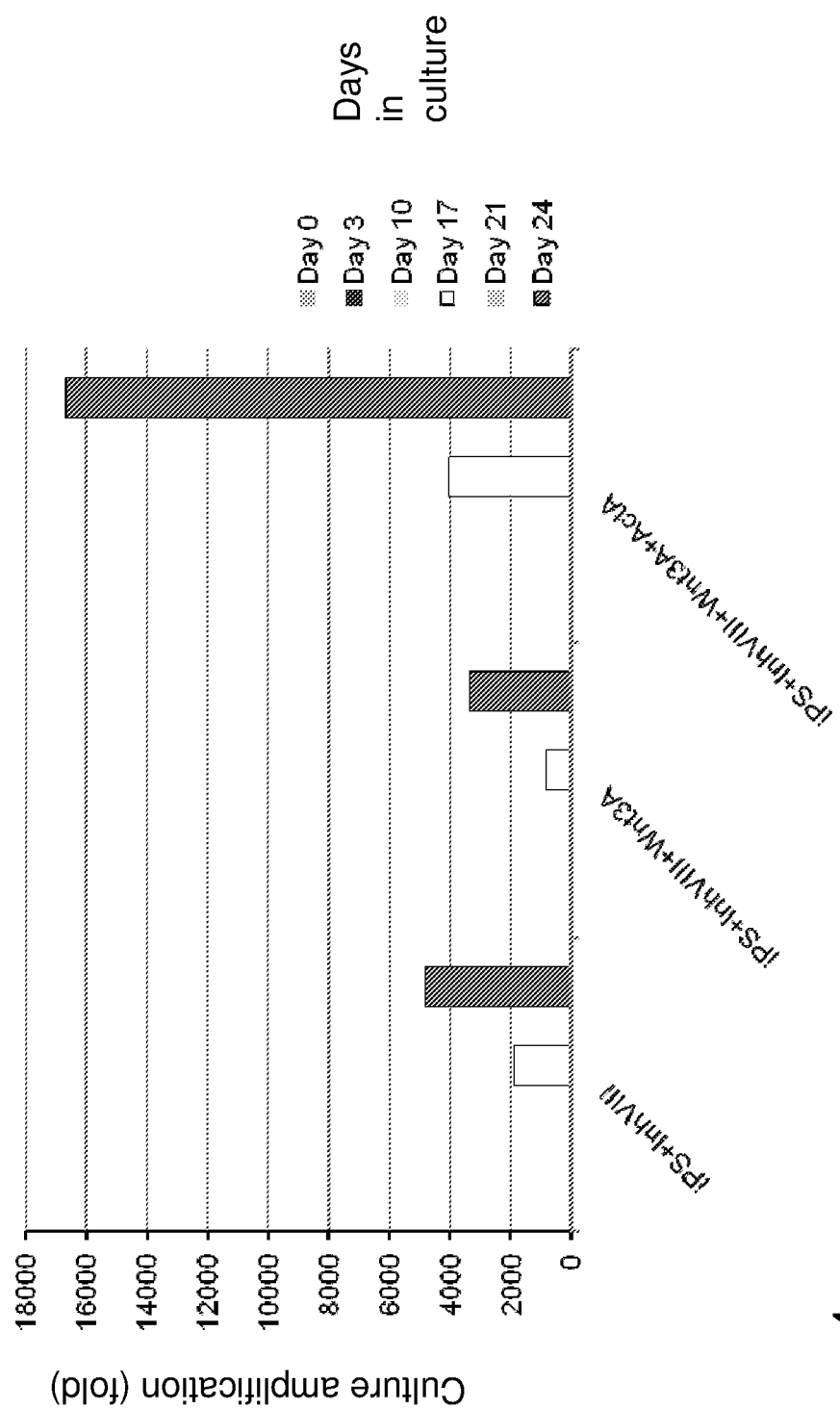

FIG. 4: GFs and GSK inhibitors are additive. Histogram representative of cumulative fold amplification during of erythroid differentiation culture of iPS line in absence or presence of Activin A.

Figure 5A:
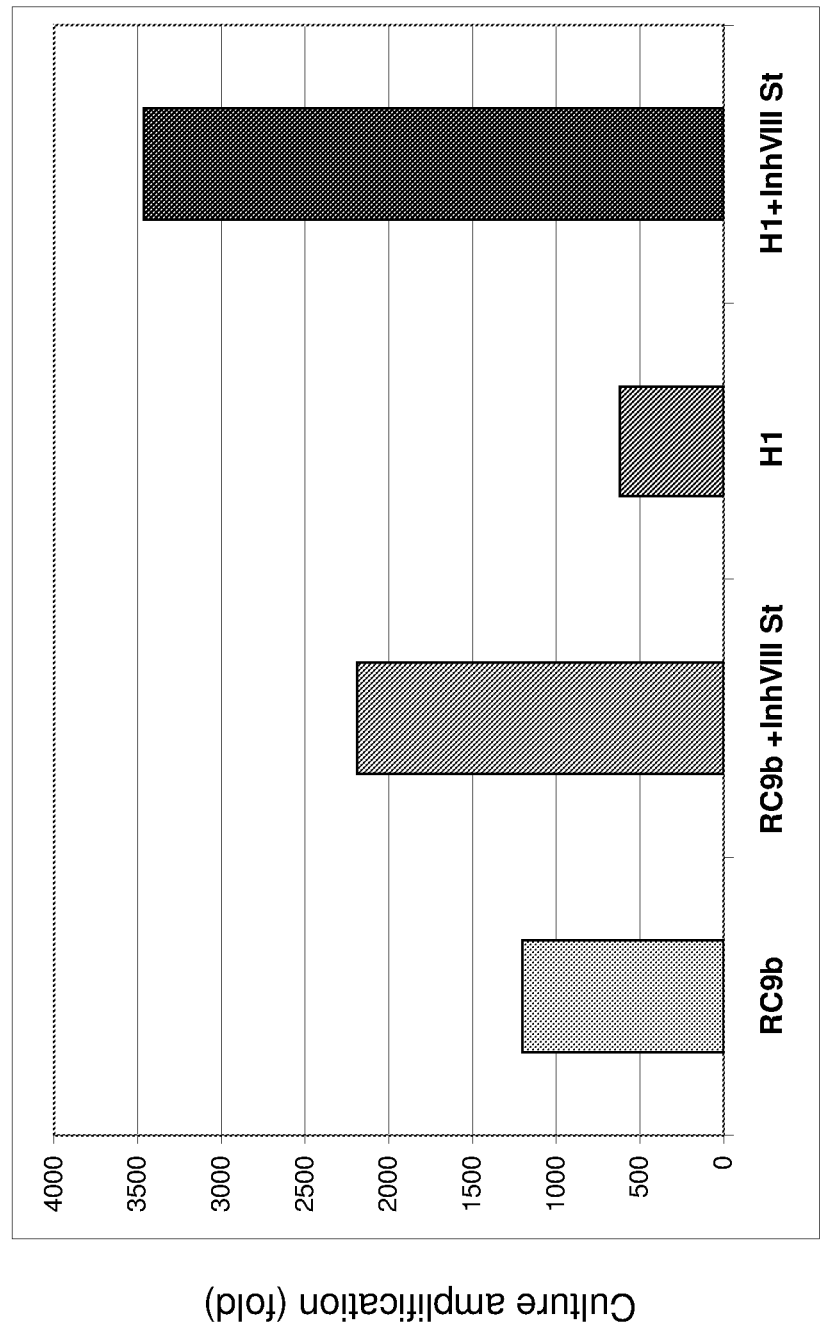
Figure 5B:
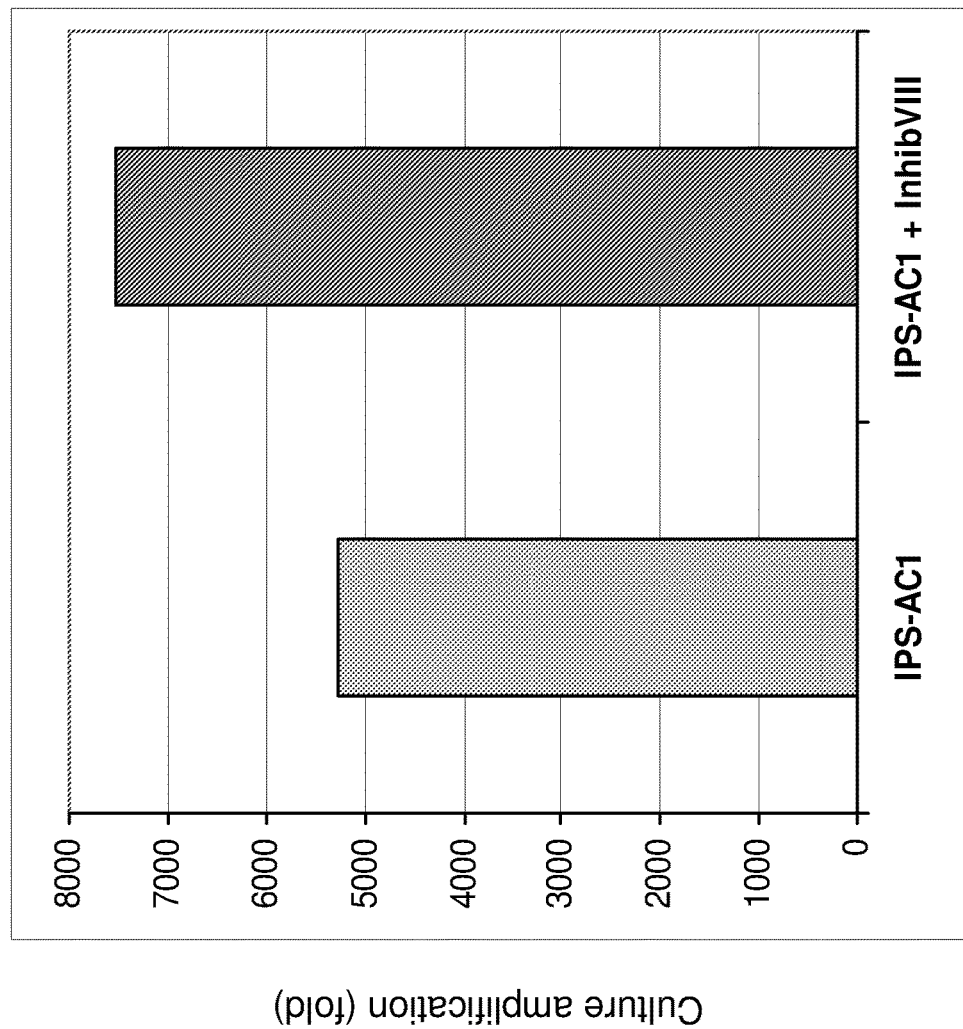

FIGS. 5A and 5B: InhibVIII increases cell numbers in multiple lines. FIG. 5A. Histogram representative of total fold amplification of erythroid differentiation culture of hESC lines RC9 and H1 in absence or presence of inhibitor VIII, FIG. 5B. Histogram representative of total fold amplification of erythroid differentiation culture of iPS line in absence or presence of inhibitor VIII, both conditions included IBMX.

Figure 6A:
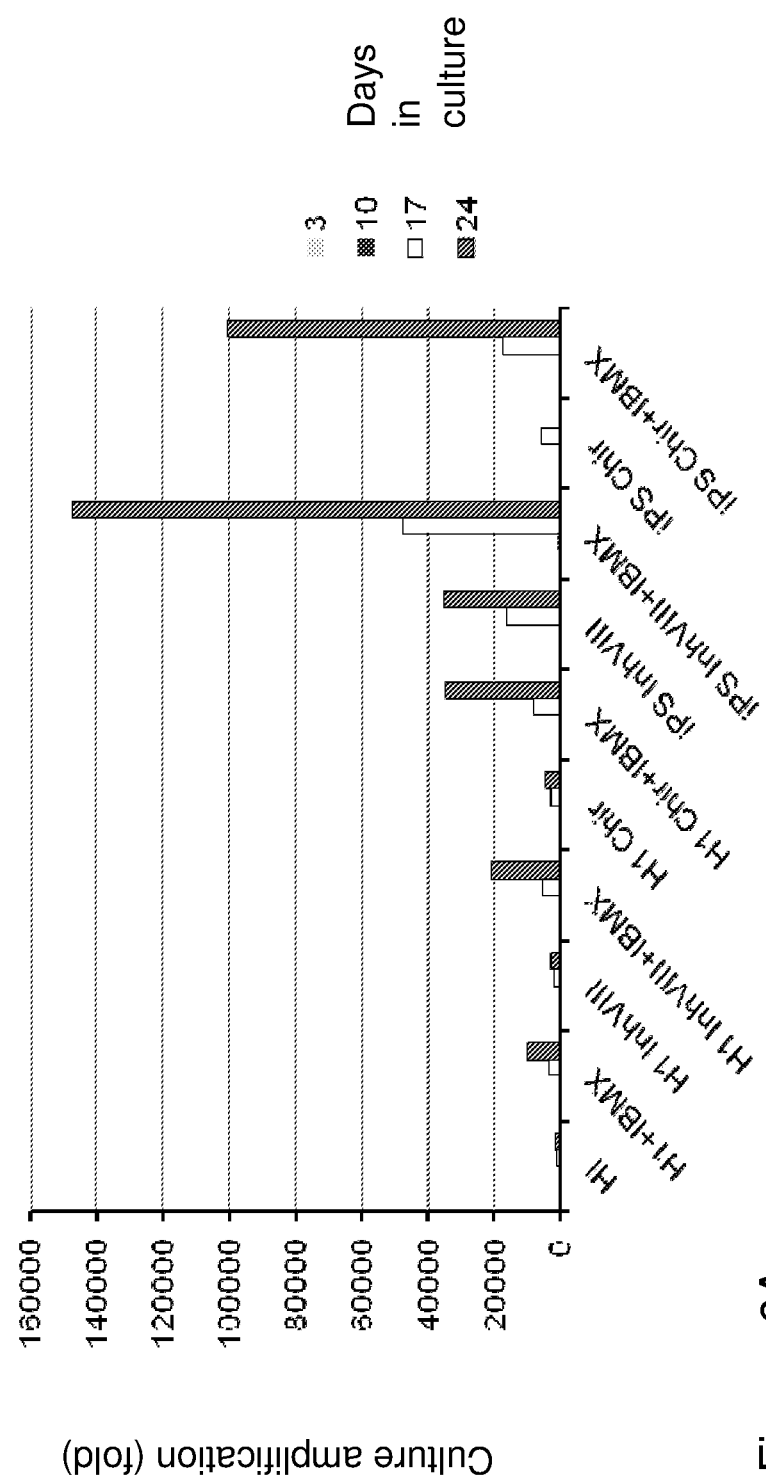
Figure 6B:
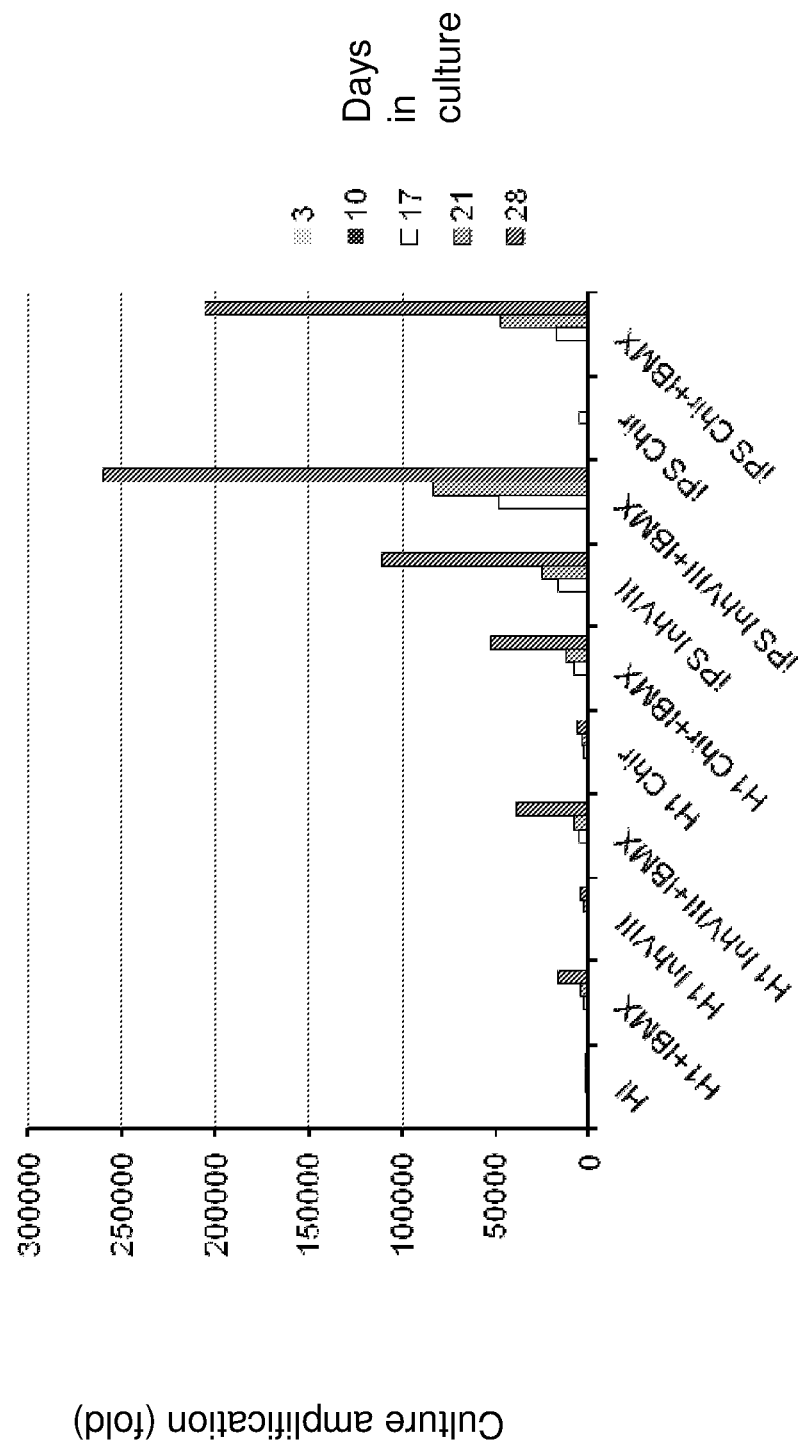

FIGS. 6A and 6B: IBMX further increases expansion. FIG. 6A. Histogram representative of cumulative fold amplification over time of erythroid differentiation culture of H1 (hESC) or hiPSC without any small molecules or with combinations of GSK3β inhibitors and IBMX using the standard option of 7 days in cytokine mix A. FIG. 6B. Histogram representative of cumulative fold amplification over time of erythroid differentiation culture of H1 (hESC) or hiPSC without any small molecule or with combinations of GSK3β inhibitors and IBMX using the prolonged period of 11 days in cytokine mix A.

Figure 7:
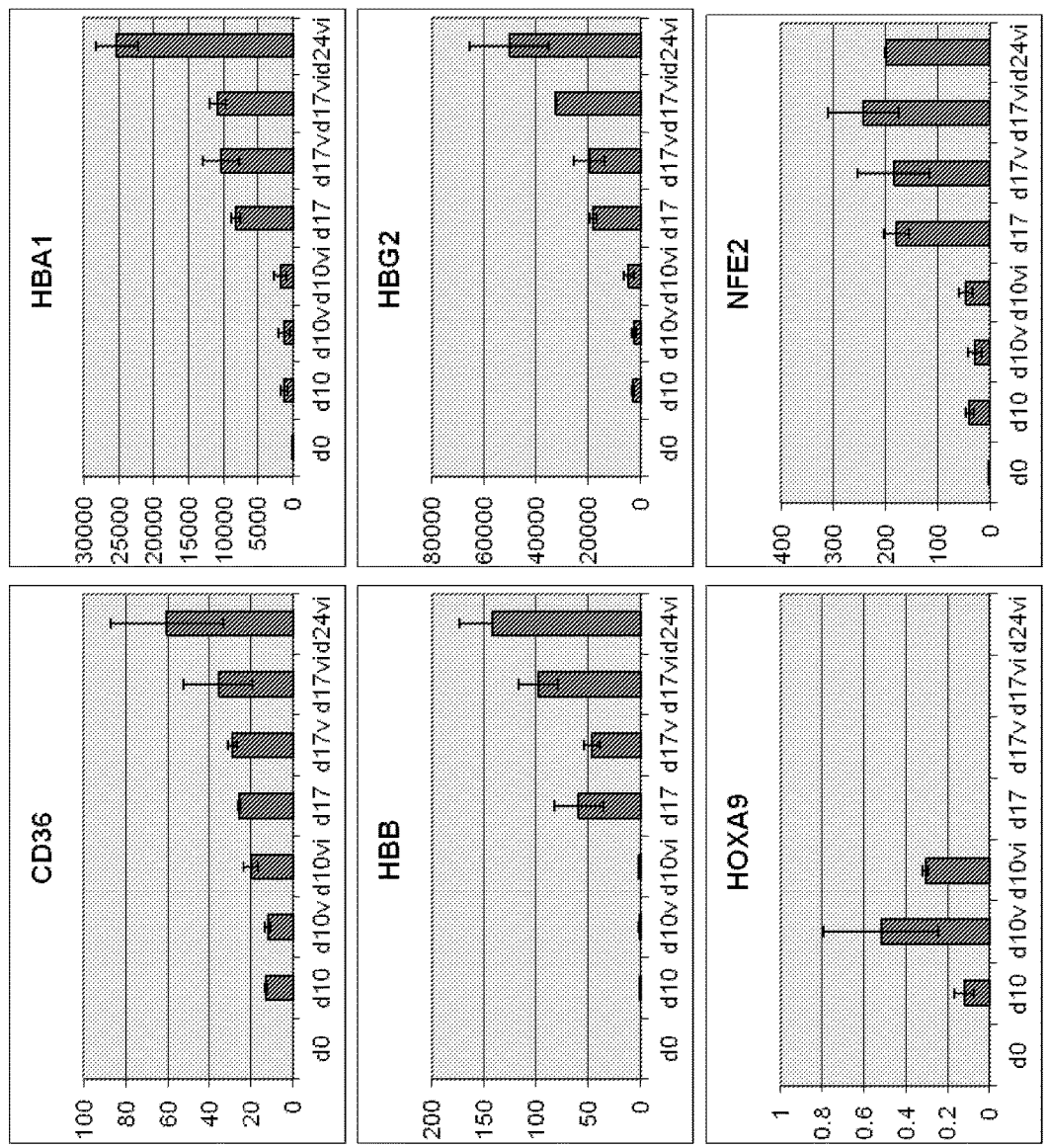

FIG. 7: InhVIII+IBMX Increase key molecular markers in iPSC. Histograms representative of mRNA expression for a set of genes involved in erythropoiesis. Expression was determined by RTqPCR of differentiating hPSCs +/− Inhibitor VIII alone or Inhibitor VIII+IBMX at day 0, 10, 17 and 24 of erythroid culture.

Figure 8A:
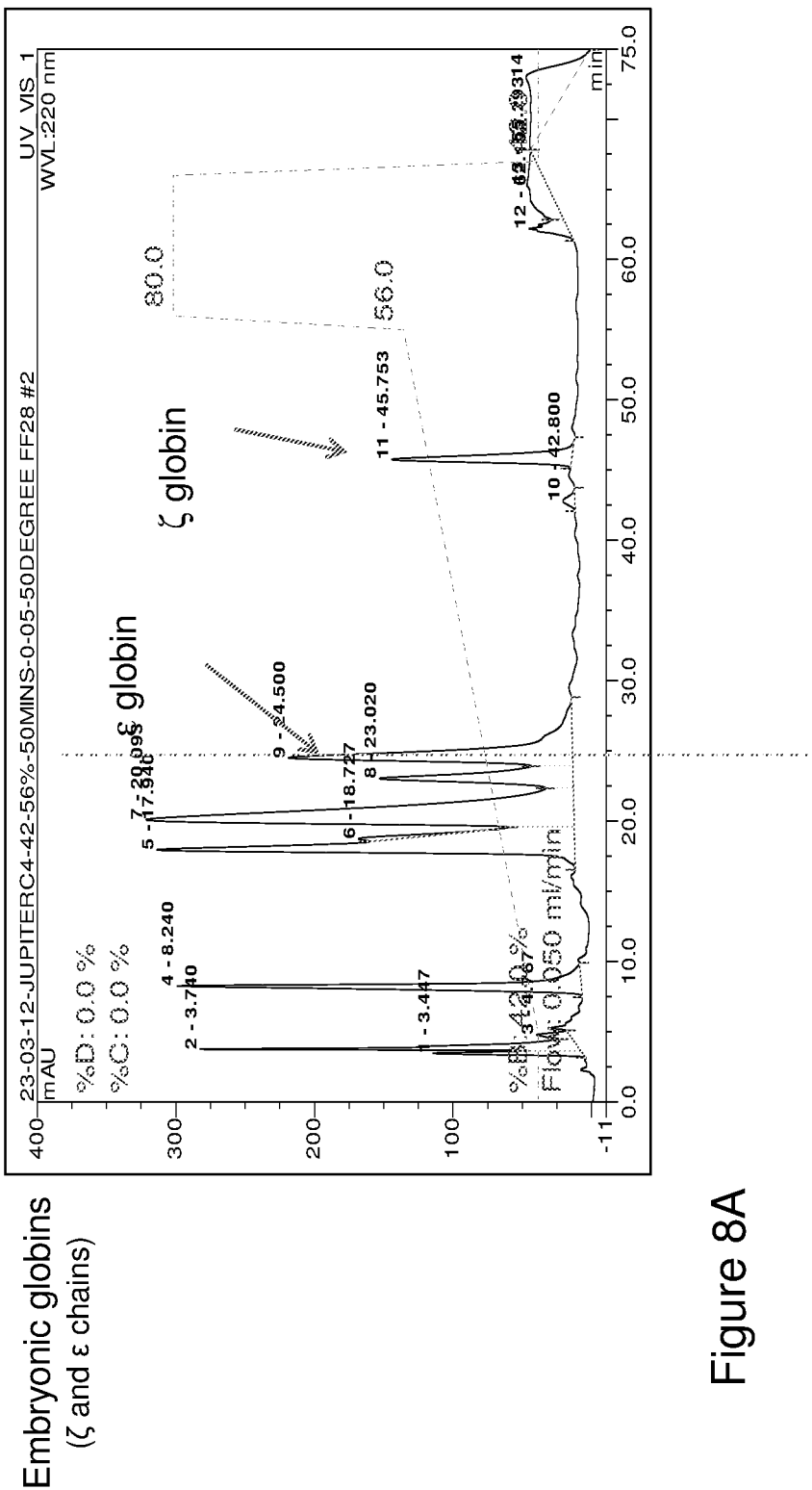
Figure 8B:
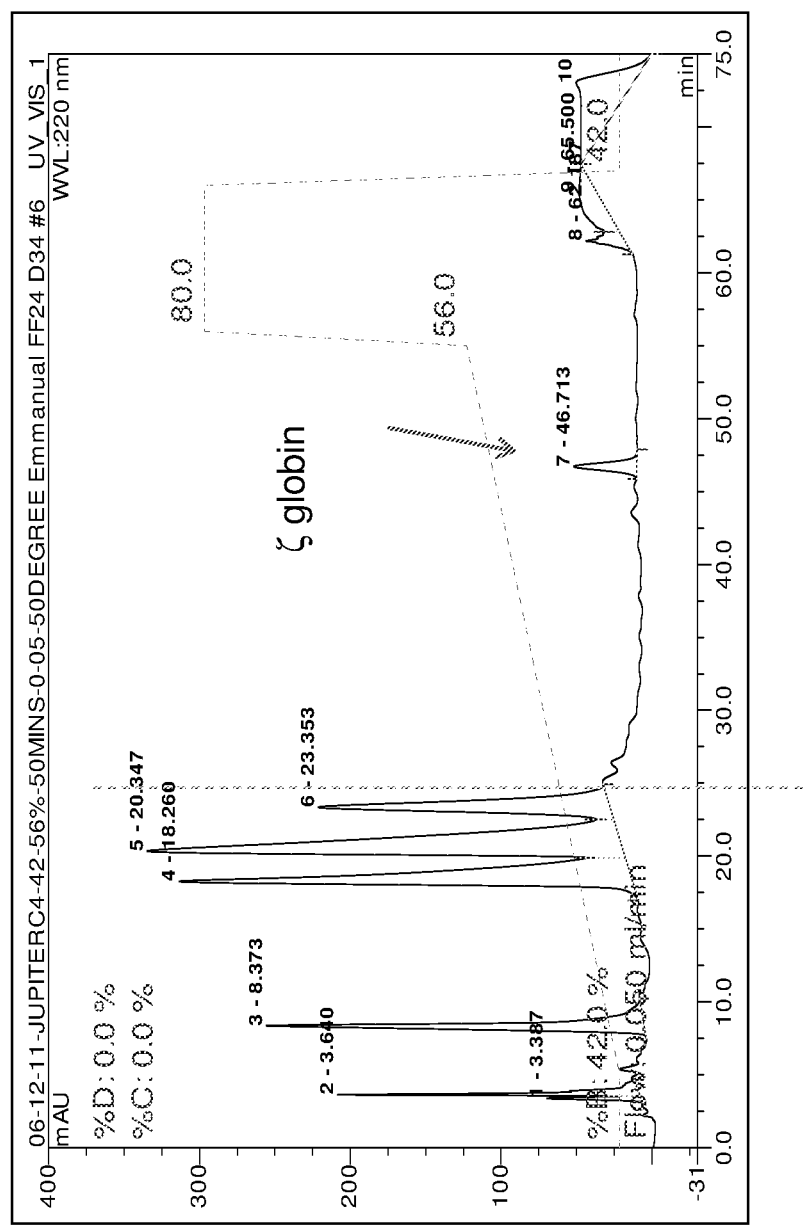
Figure 8C:
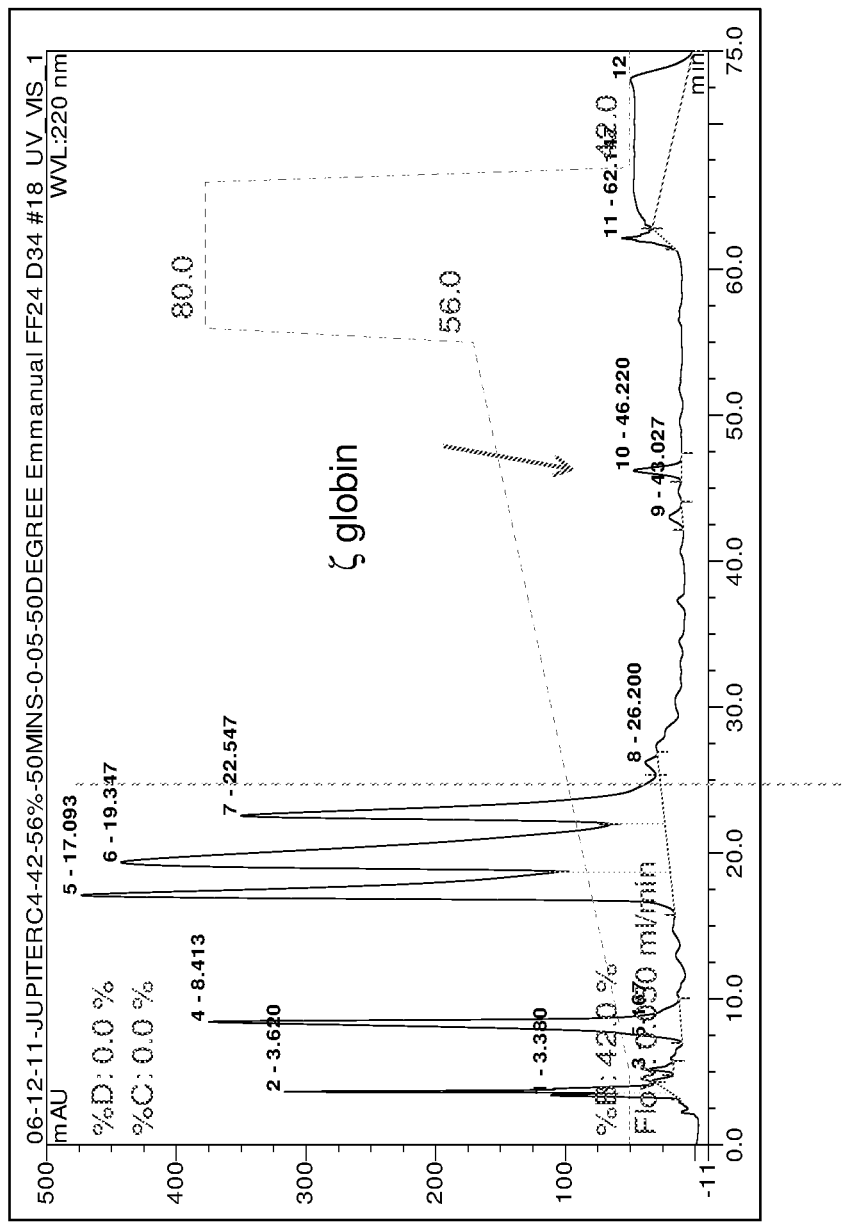
Figure 8D:
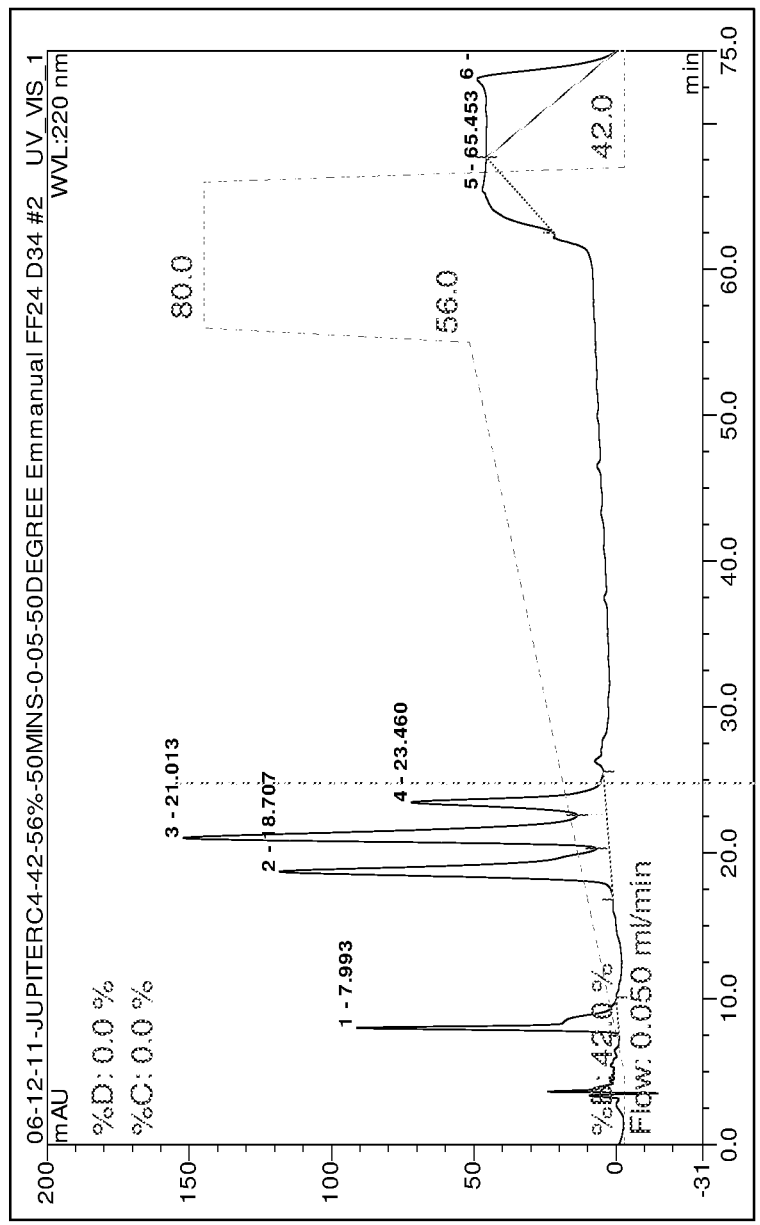

FIGS. 8A-8D: Globins are almost exclusively fetal not embryonic. HPLC analysis of the globins produced by the differentiated hPSCs. The disappearance of haemoglobin Gower 1 (ζ2 ε2 chains) is noticeable in erythroid cells derived from iPSCs (FIG. 8B) and hESCs H1 (FIG. 8C), compared with FIG. 8A, which exhibit a mixed expression of embryonic and fetal globins. The hPSC derived cells exhibit an HPLC profile similar to that obtained from control cells of fetal origin (FIG. 8D). The difference observed in globin chain may be due to some residual haemoglobin Portland (ζ2 γ2 chains).

Figure 9:
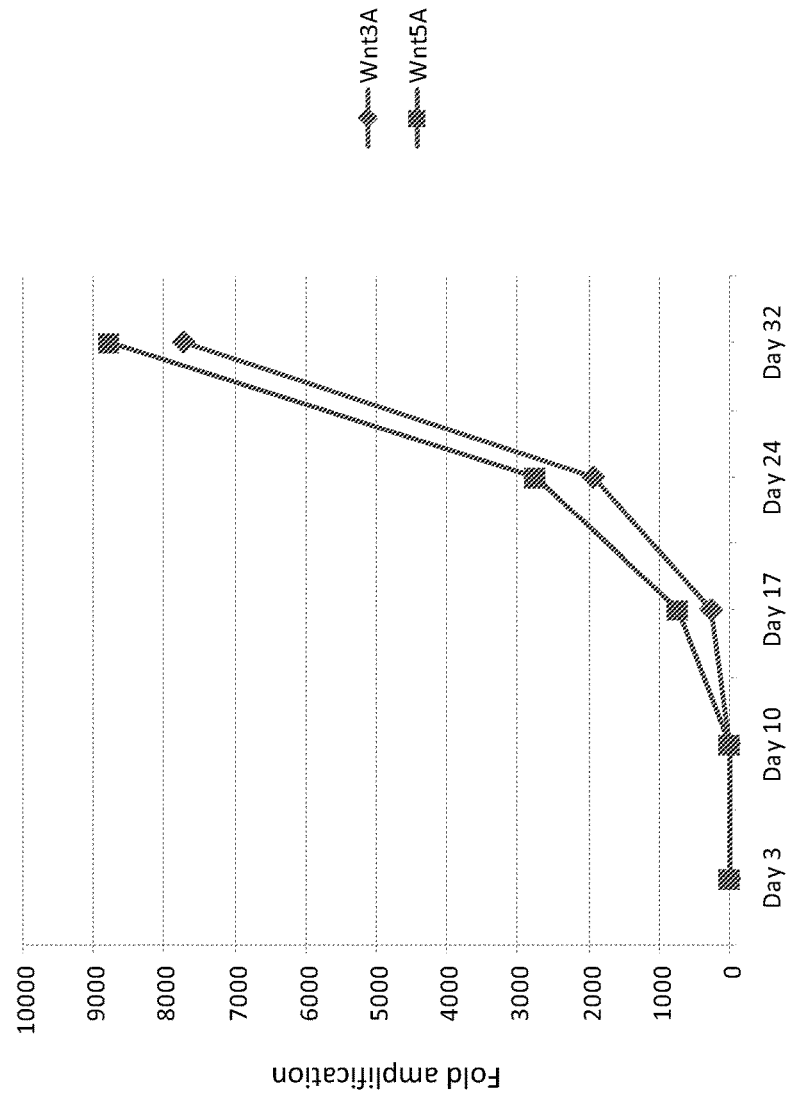

FIG. 9: Comparison of cell numbers with wnt3a vs. wnt5a.

Figure 10A:
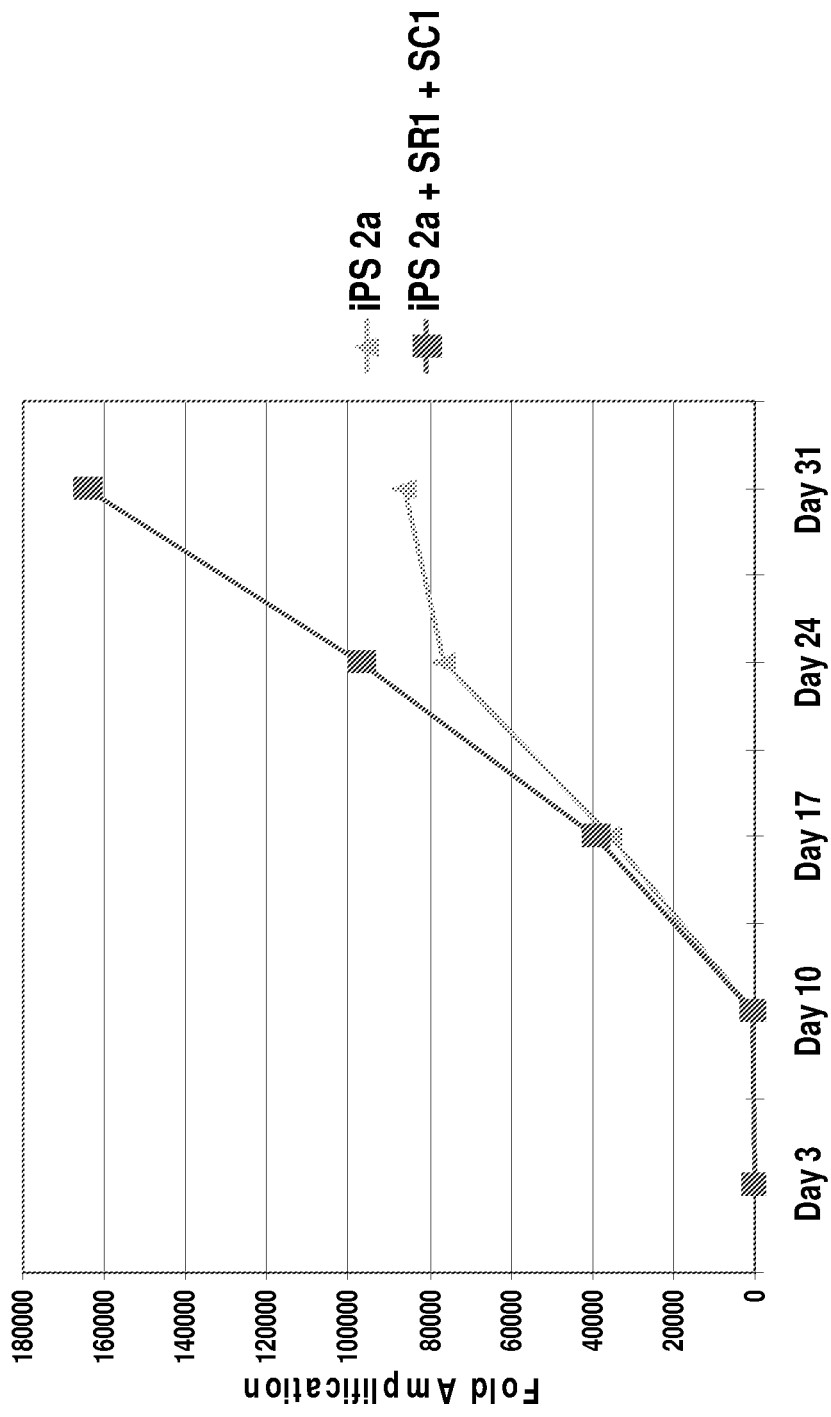
Figure 10B:
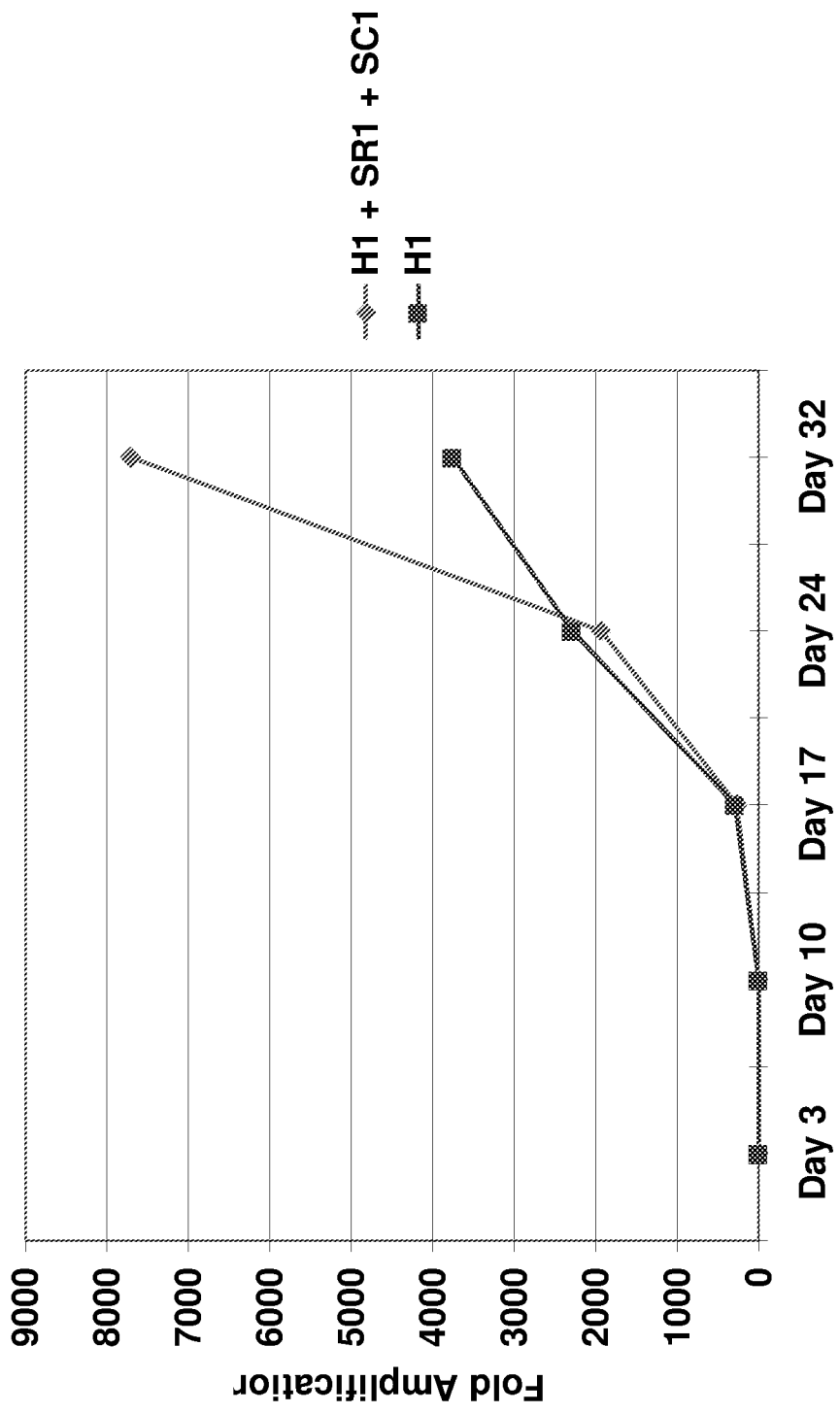

FIGS. 10A and 10B: Effect of SC1+SR1 on iPSC (FIG. 10A) or hESC (FIG. 10B) amplification during differentiation.

Figure 11:
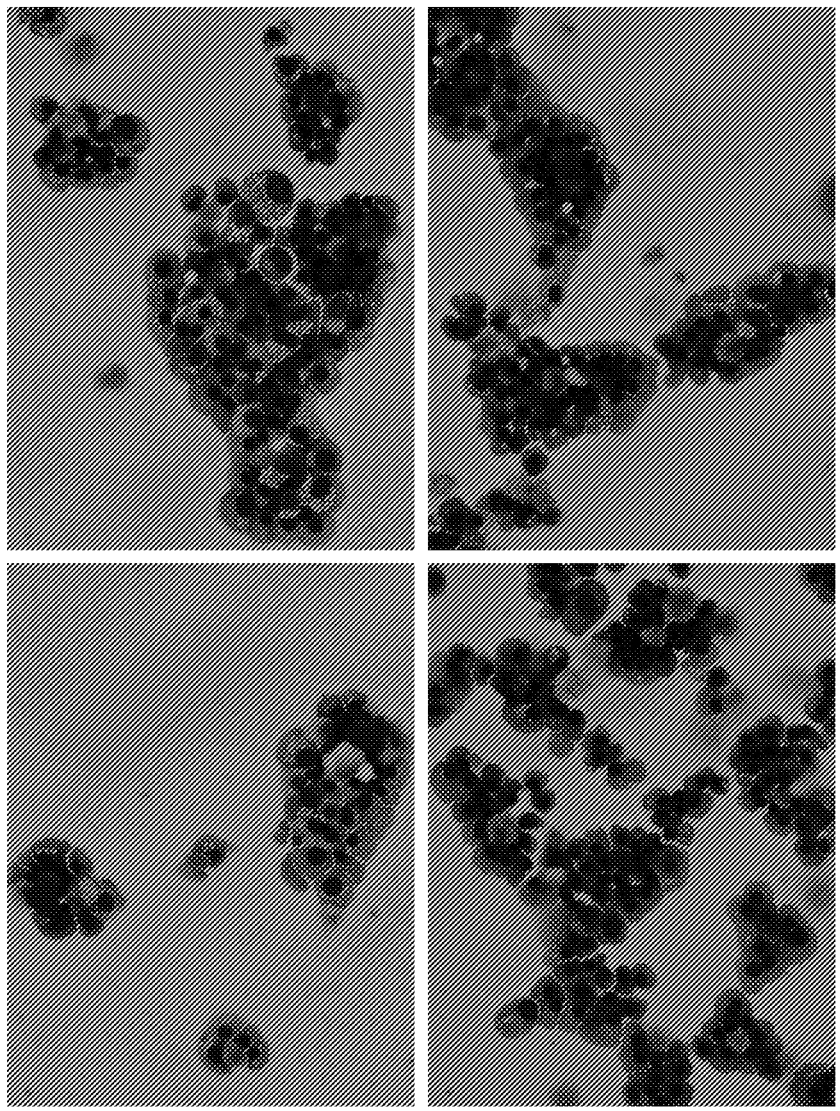

FIG. 11: Comparison of cells at day 30 after culture +/−SR1 and SC1.

Methods

The human pluripotent stem cells (hPSC) are maintained undifferentiated in Stempro medium (Life Technologies) on Cellstart (Life Technologies) and passaged approximately every 7 days, depending on their confluence, using the EZpassage tool (Life Technologies).

For differentiation, confluent hPSC are cut into squares with the EZpassage tool (Life Technologies) and plated at $500 \times 10^3$/well on Ultra low adherence six well plates (Corning) in 3 ml/well of Stemline II (Sigma) to allow them to form embryoid bodies (EBs).

On day 0 in order to induce differentiation, the following cytokines are added: Bone Morphogenic Protein 4 (BMP4) (10 ng/ml), Vascular Endothelium Growth Factor 165 (VEGF) (10 ng/ml), Wnt3A (and/or Wnt5A) (10 ng/ml), ActivinA (5 ng/ml) and Inhibitor VIII (2 μM). GSK3 Inhibitor VIII is a specific name for the Merck product (361549), it is also called AR-A014418 or N-(4-Methoxybenzyl)-N'-(5-nitro-1,3-thiazol-2-yl)urea On day 2 of differentiation (48 hours old EBs), a new set of cytokines is added in 0.5 ml/well of Stemline II; BMP4 (20 ng/ml), VEGF (30 ng/ml), Wnt3A (and/or Wnt5A) (10 ng/ml), ActivinA (5 ng/ml), Inhibitor VIII (2 μM), Fibroblast Growth Factor α (FGFα) (10 ng/ml), Stem Cell Factor (SCF) (20 ng/ml) and β-Estradiol (0.4 ng/ml).

NB: Given cytokine concentrations are always the final concentrations of freshly added cytokines—e.g. when cells are fed rather than undergoing complete media change, we add 0.5 ml of 6× cytokines to 2.5 ml already in well to give final total volume of 3 ml with 1× cytokines.

On day 3 of differentiation the EBs are washed in PBS then dissociated using 1 ml/well TrypleSelect 10λ for 10 minutes at 37° C. After addition of 10 ml of PBS, cells are centrifuged for 3 minutes at 1200 rpm, the supernatant is discarded and the cells are resuspended in 3 ml fresh Stemline II and replated at $200 \times 10^3$/well of a regular six well tissue culture plate with the following cytokines: BMP4 (20 ng/ml), VEGF (30 ng/ml), FGFα (10 ng/ml), SCF (30 ng/ml), Insulin-like Growth Factor 2 (IGF2) (10 ng/ml), Thrombopoietin (TPO) (10 ng/ml), Heparin (5 ug/ml), Iso Butyl Methyl Xanthine (IBMX) 50 μM and β-Estradiol (0.4 ng/ml).

On day 5 of differentiation a fresh set of cytokines identical to day 3 is added in 0.5 ml/well of Stemline II such that final concentrations of fresh cytokines are those stated for day 3.

On day 7 of differentiation the cells are harvested, centrifuged 3 minutes at 1200 rpm and resuspended in fresh Stemline II medium supplemented with the same set of cytokines as day 3. If the number of cells is above $500 \times 10^3$, it is advisable to split the culture as any drastic depletion or major pH increase of the medium can have major repercussion on the differentiation efficiency.

From day 7 to day 10 of differentiation the cell density should be closely monitored in order to maintain the cell number under $10^6$ per ml by adding fully supplemented media and splitting into additional wells if required.

On day 9 of differentiation a half dose of day 3 cytokines is added in 0.5 ml/well of Stemline II such that final concentrations of fresh cytokines are half those stated for day 3.

On day 10 of differentiation, the cells are centrifuged 3 minutes at 1200 rpm then re-plated in erythroid liquid culture conditions. i.e. the cells are plated at a density of $100 \times 10^3$ cells/well in 3 ml/well of Stemline II supplemented with the following cytokines: Hydrocortisone $10^{-6}$M, SCF (50 ng/ml), Flt3-Ligand (Flt3L) (16.7 ng/ml), BMP4 (6.7 ng/ml), Interleukin 3 (IL3) (6.7 ng/ml), IL11 (6.7 ng/ml), IBMX (50 μM) and Erythropoietin (EPO) 1.3 U/ml.

From day 10 to day 17 (short protocol) or 21 (extended A phase protocol), the above cytokines are renewed every 2 days, added in 0.5 ml of Stemline II, such that final concentrations of fresh cytokines are those stated for day 10.

On day 17 (short protocol) or 21 (extended A phase protocol) of differentiation the cells are centrifuged 3 minutes at 1200 rpm then re-plated at a density of $500 \times 10^3$ to $1 \times 10^6$ cells/well in 3 ml/well of IBIT medium (composed of Incomplete Iscove's Medium with stable glutamine (Biochrom AG), 1% Bovine Serum Albumin (Life Lechnologies or Sigma), 10 ug/ml Insulin, 200 ug/ml Transferrin (both from Sigma) and xeno free component lipid mixture solution 200× (Peprotech)) supplemented with the following cytokines: Hydrocortisone $10^{-6}$M, SCF (20 ng/ml), Insulin Growth Factor 1 (IGF1) (20 ng/ml), Interleukin 3 (IL3) (6.7 ng/ml), IL11 (6.7 ng/ml) and Erythropoietin (EPO) 2 U/ml.

From day 17 or 21 to day 24 or 28, a full dose of the above cytokines are renewed every 2 days, added in 0.5 ml of Stemline II. such that final concentrations of fresh cytokines are those stated for day 17 or 21.

On day 24 or 28 of differentiation the cells are centrifuged 3 minutes at 1200 rpm then re-plated at a density of $500-1000 \times 10^3$ in fresh IBIT supplemented with 4 U/ml of EPO for 2 days, followed by 5 to 10 days in IBIT medium alone. The culture medium is refreshed every 2 days by addition of fresh IBIT medium.

Analysis and Characterization

At day 10, 17 or 21 and 24 or 28, cells were analysed by flow cytometry to evaluate their hematopoietic and erythroid characteristics. The antibodies used were directed against CD31, CD34, CD36, CD41a, CD43, CD45, CD71 and CD235a (also known as glycophorin A) (BD Biosciences and eBioscience) and the cells were analysed with a BD FACSCalibur flow cytometer (BD Biosciences).

At day 17 onward, the erythroid stage of the cells was determined assessment of morphology after Rapid Romanovski staining of cytospin preparations.

At days 0, 10, 17 and 24 the expression of selected genes of interest by the differentiating cells was monitored by qRT-PCR (Taqman)

The gene panel was selected to comprise genes known to be expressed at various stages of erythropoiesis in order to evaluate the degree of differentiation of the hPSCs.

At day 24, 28 or onward the globin protein expression profile was analysed by High Pressure Liquid Chromatography to evaluate the level of switch from primitive to definitive hematopoiesis.

Results

The generation of RBCs from hPSC described herein is a sequential differentiation process aimed at mimicking in vivo erythroid development, in order to obtain a final product similar to and consistent with the biological functions of in vivo derived RBCs.

Firstly the hPSCs are encouraged to form EBs and are directed towards mesodermal germ layer specification through a balanced cocktail of BMP4, VEGF, Wnt3A (Wnt5A) and Activin A. Several dosages were tested in order to determine the best combination of cytokines to optimize conversion efficiency. Secondly, at day 2 of the EBs stage, hematopoietic lineage differentiation is primed through the increase of BMP4 and VEGF and the addition of SCF, FGFα and β-Estradiol.

After the EBs dissociation the cells are further directed towards hematopoietic differentiation through the addition on day 3 of a cytokines mix designed to favour the emergence and multiplication of hematopoietic stem cells (HSC) rather than other mesodermal lineages. At this stage, dispersed EBs will adhere to culture surface if permitted to do so, however if this adherence is inhibited by using ultra low adherence surface culture plastic (which do not support cell adherence) there is no detrimental effect on cell numbers (FIG. 1), thus this method can be executed completely in suspension culture.

HSCs are characterised in part by expression of the CD34 antigen and the maximum of CD34+ cells is generally reached between days 7 and 10, as shown in FIG. 2, CD34 can be detected in 30-80% of iPSC or hESC derived cells. Further confirmation of hematopoietic identity is provided by analysis of the CD43 antigen [Ref: Vodyanik M A, Thomson J A, Slukvin II, Blood, 2006 15; 108(6):2095-105], as shown in FIG. 2, at day 10 flow cytometry analysis shows that 50-100% of cells express this important marker. From the panel of antigens detected on the d10 cells, and notably the simultaneous presence of CD31, CD41a, CD43 and CD235a, it seems that the majority of the cells are at the hemangioblastic or post hemangioblastic stage. (FIG. 2) [Ref: Salvagiotto G et al, Exp Hematol. 2008 36(10):1377-89]. These cells at d10 are also capable of forming colonies comprising all myeloid lineages in CFU assays.

At day 17 or 21 the antigen expression profile, as well as the rapid Romanovsky staining show that the large majority of the cells are clearly erythroid, with most of them being either pro or basophilic normoblasts. At this stage the basal medium is switched to IBIT as Stemline II does not support erythroblast maturation. The corresponding cytokines cocktail has been refined to produce cells which display the highest levels of erythrocytic markers.

At day 24 or 28, 95% to 100% of the cells are erythroid as shown by the flow cytometry analysis of CD235a expression (FIG. 3). Cytospins of d24 or d28 cells show a variable distribution between the basophilic, polychromatic and orthochromatic subclasses of erythroblast, depending on the differentiation condition tested and the origin of the hPSCs used (FIGS. 3 A and B). From this point, when left in the culture conditions described in the methods, the differentiating cells evolve toward an almost homogenous population of orthochromatic normoblasts, with a small percentage of cells undergoing spontaneous enucleation.

In order to reduce the use of costly recombinant protein growth factors we investigated whether recombinant Wnt3A could be replaced with small molecule Glycogen Synthase Kinase 3β (GSK3β) inhibitors. These drugs were postulated as possible replacements for recombinant Wnt3A because of their ability to mimic sustained Wnt signalling by preventing the phosphorylation of β-catenin by GSK3β and thereby allowing the release and accumulation of active β-catenin.

The addition of GSK3β inhibitors such as Inhibitor VIII (A-A014418) or CHIR99021 (but not the less specific inhibitor BiO) during day 0 to day 3 of the differentiation protocol could not reproducibly replace Wnt3a. However, when used along with Wnt3a, these inhibitors unexpectedly caused a marked improvement in the quality and quantity of erythrocytic cells produced by our differentiation protocol as shown in FIGS. 3B and 4. Preliminary results indicated that these GSK3β inhibitors prompt a differential response from different pluripotent cell lines. Therefore, we tested multiple combinations of cytokines and inhibitors administered during different phases of the culture protocol in order to establish the best conditions for each line and importantly, the best generally applicable conditions. As shown in FIG. 3, the combination given in the method above shows a marked improvement of amplification and cell robustness at the end of the liquid culture and is applicable for both iPSC and hESC.

In H1 ESC differentiation Inhibitor VIII can replace Activin A but this effect wasn't observed in RC9 and iPSC G cell lines where the absence of Activin A markedly hinders the differentiation efficiency (FIG. 4). In order to define a method that is most generally applicable we use the combination of a GSK3β inhibitor, Wnt3A and Activin A in the early stage of differentiation which results in consistent results with all hPSC lines tested (FIGS. 5A and B). The second GSK3β inhibitor tested, CHIR99021 is more potent (0.2 μM instead of 2 μM for Inhibitor VIII) and has a stronger effect on hESC than hiPSC lines compared to Inhibitor VIII (Table 1). Additionally, increasing the period of treatment with InhVIII (d0 to d5) also increases the expansion in cell number.

cAMP and its principal target, the cAMP-dependent protein kinase A (PKA) play important roles in many biological processes including proliferation and differentiation in wide variety of cell types and can stimulate cell proliferation by activating ERKs in dividing cells through Ras-mediated activation of either B-Raf or Raf-1. Here we have shown that 3-isobutyl-1-methylxanthine (IBMX), non specific inhibitor of cAMP and cGMP phosphodiesterases which regulate the degradation of intracellular cAMP can increase cell numbers in the culture and when tested with the GSK3β inhibitor, IBMX has a synergetic effect on cell amplification (FIGS. 6A and B, Table 1). IBMX has been tested at various stages of the differentiation protocol and was found to be most effective in inducing maximum amplification when added to culture medium through out the period day 3 and 17 (Table 1).

As the cells treated with the combination of GSK3β inhibitor and IBMX appear morphologically more intact and robust, we pushed the capacity for amplification by increasing the length of the differentiation period in cytokines A mix, normally 7d between d10-17, to a total of 11d as shown in FIG. 6B the extra time allow for an additional amplification and suggests that this phase may be extended further with consequent increases in cell number.

The cells were also investigated at the molecular level at different timepoints using real time quantitative PCR to evaluate the differences of level of expression of a set of genes involved in hematopoiesis and more specifically, erythropoiesis (FIG. 7). Results from either hiPSC or hESC show that small molecules Inhibitor VIII and IBMX increase expression of globin genes and other markers characteristic of definitive hematopoiesis (HBA, HBG, HBB, Runx1, Gata2, HoxB4) as well as genes specific of different stage of erythropoiesis (HOXA9, CD36 and NFE2) and do not affect the necessary reduction in pluripotent markers.

The addition of IBMX and GSK3β inhibitors did not have any negative effect on the cells morphology and maturation compared to the control culture conditions and as small molecules are highly compatible with cGMP compliant production of in vitro generated red blood cells. The hPSCs which underwent the full differentiation process in presence of both GSK3β inhibitor and IBMX exhibit a HPLC globin profile almost similar to the cells of fetal origin with very little embryonic globins left (FIG. 8) which is a good indicator that the vast majority of the cells produced are typical of definitive hematopoiesis. However, only a small % of the cells undergo spontaneous enucleation in the final stages of culture.

Inclusion of 2 additional small molecules improves quality and amplification of cells. On day 5 of differentiation a fresh set of cytokines identical to day 3 is added in 0.5 ml/well of Stemline II. The small molecule StemRegenin1 (SR1) (Cellagen Technology) at a final concentration of 1 μM is added along the cytokines. On days 14 the small molecule Pluripotin (SC1) (Stemgent) is added along the cytokines for a final concentration of 500 nM. On days 16 the small molecule Pluripotin (SC1) (Stemgent) is added along the cytokines for a final concentration of 250 nM The addition of SR1 at day 5 and SC1 at days 14 and 16 allow for a greater rate of cell amplification in the late stage of the method (FIG. 2). The cells are also sturdier and less prone to lysis (FIG. 3). These small molecules were tested because of their published properties on CD34+ amplification (SR1) or maintenance of pluripotency (SC1) (refs below) but they have not previously been implicated in erythroid development. Their effect is strongly dependant of the timing of administration.

Summary

Here we present a differentiation protocol which uses suspension based liquid culture throughout and is therefore scalable, it also achieves a degree of efficiency high enough to avoid the need for any purification step (>80% HPC at d10 and >90% erythroid series by d24). The method supports a considerable amplification of cell numbers as they differentiate to RBCs (up to 350,000 fold d0-24) which is in excess of previously reported methods, even those using HoxB4 as an amplifying agent [REFS]. The method is suitable for either human induced pluripotent stem cells (iPSC) or embryonic stem cells (hESC) referred to together as human pluripotent stem cells (hESC), including hESC lines that have been derived under fully GMP compliant and licensed conditions. Furthermore, the cells reach the orthochromatic normoblast stage of erythropoiesis and display characteristics of definitive hematopoiesis (including the shut off of embryonic globins and expression of Aγ globin). As another step towards scale-up of the process we have also ensured that the protocol starts with hPSC that have been maintained for many passages in feeder-free culture using GMP-compliant reagents amenable to large scale mechanised production.

This differentiation method can be used for the efficient differentiation of human pluripotent SC including hiPSC and hESC.

Actvin A is required for efficient differentiation of iPSC

An increased dose of Activin A doesn't have any beneficial effect (data not shown)

A prolonged pulse of Inhibitor VIII (d0-5) increases the yield of differentiated cells (iPSC or hESC)

The combination of Inhibitor VIII or CHIR99021 and IBMX is synergistic, but BiO, a less specific GSK3 inhibitor does not have this effect.

A prolonged culture in cytokine mix A (d10-21) allows for an increased yield of differentiated cells Combination of the tested parameters has enabled us to maximize the yield erythroid cells from hPSC to the point where we have achieved 350×10e3 erythroid cells per hPSC. This expansion is equivalent to 1 unit of RBC concentrate (2×10e12 cells) per 6×10e6 iPSC which could be harvested from less than 3 wells of a 6 well plate.

This protocol has been optimized using PSC that had previously been maintained on GMP grade cell free substrate (CellStart, Life Technologies) in GMP-grade serum free medium (StemPro, Life Technologies) and unlike many other protocols which use feeder maintained PSC, it is fully compatible with GMP-grade manufacturing.

TABLE 1 table summarizing results obtained when comparing side by side the effect of the addition of GSK3β inhibitors, IBMX or both on the overall amplification of differentiating erythropoietic cultures of hPSCs. The side by side comparison within each experiment allow the assessment of the direct effect of the compound tested without interference from other parameters like quality of initial hPSCs culture, hPCSs passage number, experimenter, activity of cytokines used or other equipment inconsistency. Results consistently show a positive effect of Inhibitor VIII and IBMX. The gain provided by a prolonged period in cytokine mix A is indicated in the bold italicised columns.

| Experiment reference | hPSCs | GSK3b inhibitor | Other Additions | 0-3 | 0-10 | 0-17 | 0-21 | 0-24 | 0-28 |
|---|---|---|---|---|---|---|---|---|---|
| FF22 | RC9b | | | 3 | 17 | 507 | | 1201 | |
| | RC9b | InhVIII | | 5 | 35 | 1425 | | 2195 | |
| | H1 | | | 2 | 8 | 301 | | 620 | |
| | H1 | InhVIII | | 2 | 28 | 1702 | | 3464 | |
| FF23 | RC9b | | | 2 | 9 | 153 | | 164 | |
| | RC9b | InhVIII | | 5 | 33 | 999 | | 1778 | |
| | H1 | | | 5 | 58 | 3922 | | 52162 | |
| | H1 | InhVIII | | 10 | 115 | 7688 | | 94558 | |

TABLE 1-continued

| | | | | | | | | | |
|---|---|---|---|---|---|---|---|---|---|
| FF28 | iPS | InhVIII | | 7 | 36 | 2804 | *6422* | 3365 | *8413* |
| | iPS | InhVIII | InhVIII d3 | 7 | 84 | 5322 | *6386* | 7131 | *6067* |
| | iPS | InhVIII | IBMX d3-16 | 7 | 77 | 7002 | *15894* | 23106 | *42120* |
| | iPS | InhVIII | InhVIII d3 + IBMX d3-16 | 7 | 121 | 6291 | *14407* | 36804 | *78807* |
| FF29 | H1 | | | 2 | 25 | 1000 | *1200* | 1710 | *1320* |
| | H1 | | IBMX d3-16 | 2 | 45 | 3122 | *4089* | 10114 | *16276* |
| | H1 | InhVIII | | 3 | 60 | 1737 | *2518* | 2866 | *4231* |
| | H1 | InhVIII | IBMX d3-16 | 3 | 111 | 5236 | *8064* | 20632 | *38789* |
| | H1 | CHIR99021 | | 4 | 74 | 2820 | *3835* | 4483 | *6174* |
| | H1 | CHIR99021 | IBMX d3-16 | 4 | 140 | 7738 | *11994* | 34743 | *52292* |
| | iPS | InhVIII | | 5 | 424 | 16162 | *24405* | 35396 | *111043* |
| | iPS | InhVIII | IBMX d3-16 | 5 | 692 | 47474 | *83080* | 147645 | *260040* |
| | iPS | CHIR99021 | | 8 | 227 | 5597 | *nd* | nd | *nd* |
| | iPS | CHIR99021 | IBMX d3-16 | 8 | 484 | 17224 | *46850* | 100418 | *205204* |
| AC | RC9 | InhVIII | no IL11 d10 to d23 | 2 | 45 | 2173 | | 9321 | |
| | RC9 | InhVIII | IL11 d10 to d23 | 2 | 45 | 3046 | | 13861 | |
| | RC9b | InhVIII | | 2 | 49 | 6106 | | 12822 | |
| | RC9b | InhVIII | IBMX d3-16 | 2 | 71 | 10749 | | 64497 | |
| | RC9b | InhVIII | 6 wells plate, IBMX d3-16 | 1 | 135 | 39399 | | 327015 | |
| | RC9b | InhVIII | T150, IBMX d3-16 | 1 | 116 | 28649 | | 212002 | |
| LM | iPS | | IBMX d3-16 | 2 | 6 | 776 | | 5273 | |

The invention claimed is:

1. A method of inducing the differentiation of embryonic stem cells or induced pluripotent stem cells into erythroid cells, said method comprising:
   contacting the embryonic stem cells or induced pluripotent stem cells with BMP4, VEGF, Wnt3A, ActivinA and a GSK3β inhibitor under conditions which induce the formation of embryoid bodies;
   contacting the embryoid bodies with BMP4, VEGF, Wnt3A, ActivinA, FGF-α, SCF, β-estradiol and a GSK3β inhibitor; and
   dissociating the embryoid bodies to form dissociated embryoid bodies; and
   contacting the dissociated embryoid bodies with BMP4, VEGF, FGF-α, SCF, IGF2, TPO, heparin, β-estradiol and IBMX and then with hydrocortisone, SCF, Flt3L, BMP4, IL3, IL11, EPO and IBMX,
   to yield erythroid cells,
   wherein the GSK3β inhibitor is Inhibitor VIII or CHIR99021.

2. The method of claim 1, wherein the erythroid cells are characterised by expression of one or more haematopoietic/erythroid markers selected from the group consisting of: CD31; CD34; CD36; CD41a; CD43; CD45; CD71; and CD235a.

3. The method of claim 1, wherein the method is free of feeder cells.

4. The method of claim 1, wherein the step of contacting the embryonic stem cells or induced pluripotent stem cells with BMP4, VEGF, Wnt3A, ActivinA and a GSK3β inhibitor under conditions which induce the formation of embryoid bodies is carried out for 1, 2 or 3 days.

5. The method of claim 1, wherein the step of contacting the embryonic stem cells or induced pluripotent stem cells with BMP4, VEGF, Wnt3A, ActivinA and a GSK3β inhibitor under conditions which induce the formation of embryoid bodies is carried out for 2 days.

6. The method of claim 1, wherein the step of contacting the embryoid bodies with BMP4, VEGF, Wnt3A, ActivinA, FGF-α, SCF, β-estradiol and a GSK3β inhibitor is carried out for 0.5, 1 or 2 days.

7. The method of claim 1, wherein the step of contacting the embryoid bodies with BMP4, VEGF, Wnt3A, ActivinA, FGF-α, SCF, β-estradiol and a GSK3β inhibitor is carried out for 1 day.

8. The method of claim 1, wherein the step of contacting the dissociated embryoid bodies with BMP4, VEGF, FGF-α, SCF, IGF2, TPO, heparin, β-estradiol and IBMX is carried out for 1, 2 or 3 days.

9. The method of claim 1, wherein the step of contacting the dissociated embryoid bodies with BMP4, VEGF, FGF-α, SCF, IGF2, TPO, heparin, β-estradiol and IBMX is carried out for 2 days.

10. The method of claim 1, wherein the step of contacting the dissociated embryoid bodies with hydrocortisone, SCF, Flt3L, BMP4, IL3, IL11, EPO and IBMX is carried out for 4, 5, 6, 6.5, 7, 7.5, 8, 9, 10, 10.5, 11, 11.5, 12, 13 or 14 days.

11. The method of claim 1, wherein the step of contacting the dissociated embryoid bodies with hydrocortisone, SCF, Flt3L, BMP4, IL3, IL11, EPO and IBMX is carried out for 7 days.

12. The method of claim 1, wherein, in the step of contacting the embryonic stem cells or induced pluripotent stem cells with BMP4, VEGF, Wnt3A, ActivinA and a GSK3β inhibitor under conditions which induce the formation of embryoid bodies, the embryonic stem cells or induced pluripotent stem cells are contacted with: BMP4 at a concentration of 10 ng/ml; VEGF at a concentration of 10 ng/ml; Wnt3A at a concentration of 10 ng/ml; ActivinA at a concentration of 5 ng/ml; and the GSK3β inhibitor at a concentration of 2 μM.

13. The method of claim 1, wherein, in the step of contacting the embryoid bodies with BMP4, VEGF, Wnt3A, ActivinA, FGF-α, SCF, β-estradiol and a GSK3β inhibitor, the embryoid bodies with: BMP4 at a concentration of 20 ng/ml; VEGF at a concentration of 30 ng/ml; Wnt3A at a concentration of 10 ng/ml; ActivinA at a concentration of 5 ng/ml; FGF-α at a concentration of 10 ng/ml; SCF at a concentration of 20 ng/ml; β-estradiol at a concentration of 0.4 ng/ml; and the GSK3β inhibitor at a concentration of 2 µM.

14. The method of claim 1, wherein, in the step of contacting the dissociated embryoid bodies with BMP4, VEGF, FGF-α, SCF, IGF2, TPO, heparin, β-estradiol and IBMX, the dissociated embryoid bodies with: BMP4 at a concentration of 20 ng/ml; VEGF at a concentration of 30 ng/ml; FGF-α at a concentration of 10 ng/ml; SCF at a concentration of 30 ng/ml; IGF2 at a concentration of 10 ng/ml; TPO at a concentration of 10 ng/ml; heparin at a concentration of 5 µg/ml; β-estradiol at a concentration of 0.4 ng/ml; and IBMX at a concentration of 50 µM.

15. The method of claim 1, wherein, in the step of contacting the dissociated embryoid bodies with hydrocortisone, SCF, Flt3L, BMP4, IL3, IL11, EPO and IBMX, the dissociated embryoid bodies with: hydrocortisone at a concentration of 1 µM; SCF at a concentration of 50 ng/ml; Flt3L at a concentration of 16.7 ng/ml; BMP4 at a concentration of 6.7 ng/ml; IL3 at a concentration of 6.7 ng/ml; IL11 at a concentration of 6.7 ng/ml; EPO at a concentration of 1.3 U/ml; and IBMX at a concentration of 50 µM.

16. The method of claim 1, further comprising a step of contacting the yielded erythroid cells with hydrocortisone, SCF, IGF1, IL3, Il11 and EPO.

17. The method of claim 16, wherein the step of contacting the yielded erythroid cells with hydrocortisone, SCF, IGF1, IL3, Il11 and EPO is carried out for 5, 6, 6.5, 7, 7.5 or 8 days.

18. The method of claim 16, wherein the step of contacting the yielded erythroid cells with hydrocortisone, SCF, IGF1, IL3, Il11 and EPO is carried out for 7 days.

19. The method of claim 16, wherein, in the step of contacting the yielded erythroid cells with hydrocortisone, SCF, IGF1, IL3, Il11 and EPO, the yielded erythroid cells are contacted with: hydrocortisone at a concentration of 1 µM; SCF at a concentration of 20 ng/ml; IGF1 at a concentration of 20 ng/ml; IL3 at a concentration of 6.7 ng/ml; IL11 at a concentration of 6.7 ng/ml; and EPO at a concentration of 2 U/ml.

* * * * *

UNITED STATES PATENT AND TRADEMARK OFFICE
CERTIFICATE OF CORRECTION

PATENT NO.        : 9,677,051 B2
APPLICATION NO.   : 14/415856
DATED             : June 13, 2017
INVENTOR(S)       : Mountford et al.

It is certified that error appears in the above-identified patent and that said Letters Patent is hereby corrected as shown below:

In the Claims

Column 25, Claim 13, Line 1: Please correct "the embryoid bodies with"
   to read -- the embryoid bodies are contacted with --
Claim 14, Line 11: Please correct "embryoid bodies with"
   to read -- embryoid bodies are contacted with --
Claim 15, Line 21: Please correct "embryoid bodies with"
   to read -- embryoid bodies are contacted with --

Signed and Sealed this
Twelfth Day of June, 2018

Andrei Iancu
*Director of the United States Patent and Trademark Office*